US011542542B2

(12) United States Patent
Lease

(10) Patent No.: US 11,542,542 B2
(45) Date of Patent: Jan. 3, 2023

(54) ANTISENSE FINGERLOOP DNAS AND USES THEREOF

(71) Applicant: Ohio State Innovation Foundation, Columbus, OH (US)

(72) Inventor: Richard A. Lease, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 295 days.

(21) Appl. No.: 16/631,937

(22) PCT Filed: Jul. 18, 2018

(86) PCT No.: PCT/US2018/042739
§ 371 (c)(1),
(2) Date: Jan. 17, 2020

(87) PCT Pub. No.: WO2019/018555
PCT Pub. Date: Jan. 24, 2019

(65) Prior Publication Data
US 2020/0224252 A1 Jul. 16, 2020

Related U.S. Application Data

(60) Provisional application No. 62/562,105, filed on Sep. 22, 2017, provisional application No. 62/533,857, filed on Jul. 18, 2017.

(51) Int. Cl.
*C12Q 1/6816* (2018.01)
*C12N 15/70* (2006.01)
*C12N 15/74* (2006.01)

(52) U.S. Cl.
CPC .......... *C12Q 1/6816* (2013.01); *C12N 15/70* (2013.01); *C12N 15/74* (2013.01); *C12N 2800/10* (2013.01)

(58) Field of Classification Search
CPC ...... C12Q 1/68; C12Q 1/6813; C12Q 1/6876; C12N 15/113
See application file for complete search history.

(56) References Cited

U.S. PATENT DOCUMENTS

| | | | | |
|---|---|---|---|---|
| 5,424,413 A | * | 6/1995 | Hogan | C12N 15/1068 435/6.1 |
| 5,576,208 A | * | 11/1996 | Monia | C07K 14/82 435/375 |
| 2003/0129611 A1 | * | 7/2003 | Bao | C12Q 1/6818 536/24.3 |
| 2014/0315211 A1 | * | 10/2014 | Sugino | C12Q 1/686 435/6.12 |
| 2016/0152980 A1 | | 6/2016 | Cullen et al. | |
| 2020/0224252 A1 | * | 7/2020 | Lease | C12N 15/74 |

OTHER PUBLICATIONS

Baker et al., In vitro quantification of specific microRNA using molecular beacons. Nucleic Acids Research 40(2) : e13 (Year: 2012).*
Broude et al., Nucleic Acids Research 29(19) :e92 (Year: 2001).*
Broude, N.E.,Trends in Biotechnology 20(6) : 249 (Year: 2002).*
Li et al., Real-Time Polymerase Chain Reaction MicroRNA Detection Based on Enzymatic Stem-Loop Probes Ligation. Analytical Chemistry 81 : 5446-5451 (Year: 2009).*
Maxwell et al., Self-Assembled Nanoparticle Probes for Recognition and Detection of Biomolecules. JACS 124: 9606-9612 (Year: 2002).*
Ronaghi et al., PCR-Introduced Loop Structure as Primer in DNA Sequencing. BioTechniques 25(5) : 876 (Year: 1998).*
Tong et al., Science China : Life Sciences 55(10) : 843-861 (Year: 2012).*
Tyagi et al., Multicolor molecular beacons for allele discrimination. Nature Biotechnology 16 :49 (Year: 1998).*
International Search Report and Written Opinion issued by the International Searching Authority (ISA/US) in PCT Application No. PCT/US2018/042739 dated Sep. 26, 2018. 11 pages.
Lahiry, Ashwin, et al. "Retargeting a dual-acting sRNA for multiple mRNA transcript regulation." ACS synthetic biology 6.4 (2017): 648-658.
Kawamoto, Hiroshi, et al. "Base-pairing requirement for RNA silencing by a bacterial small RNA and acceleration of duplex formation by Hfq." Molecular microbiology 61.4 (2006): 1013-1022.
Broude, Natalia E., et al. "DNA microarrays with stem-loop DNA probes: preparation and applications." Nucleic acids research 29.19 (2001): 1-11.
Afroz, T., Biliouris, K., Kaznessis, Y., & Beisel, C. L. (2014). Bacterial sugar utilization gives rise to distinct single-cell behaviours. Molecular microbiology, 93(6), 1093-1103.
Atsumi, S., Cann, A. F., Connor, M. R., Shen, C. R., Smith, K. M., Brynildsen, M. P., . . . & Liao, J. C. (2008). Metabolic engineering of *Escherichia coli* for 1-butanol production. Metabolic engineering, 10(6), 305-311.
Beisel, C. L., & Storz, G. (2011). The base-pairing RNA spot 42 participates in a multioutput feedforward loop to help enact catabolite repression in *Escherichia coli*. Molecular cell, 41(3), 286-297.
Beisel, C. L., Updegrove, T. B., Janson, B. J., & Storz, G. (2012). Multiple factors dictate target selection by Hfq-binding small RNAs. The EMBO journal, 31(8), 1961-1974.
Bolivar, F., Rodriguez, R. L., Greene, P. J., Betlach, M. C., Heyneker, H. L., Boyer, H. W., . . . & Falkow, S. (1977). Construction and characterization of new cloning vehicle. II. A multipurpose cloning system. Gene, 2(2), 95-113.

(Continued)

*Primary Examiner* — Ethan C Whisenant
(74) *Attorney, Agent, or Firm* — Meunier Carlin & Curfman LLC

(57) ABSTRACT

The present disclosure relates to improved methods for detecting nucleic acids using DNA fingerloop stem loop structures, wherein the DNA fingerloop stem loop structures diminish base pairing of a detection probe to a mismatched target nucleic acid. The present disclosure also relates to improved methods for amplifying nucleic acids. Further disclosed are chimeric fingerloop DNAs for use in methods for modulating protein expression levels and/or RNA stability.

10 Claims, 17 Drawing Sheets

Specification includes a Sequence Listing.

(56) References Cited

OTHER PUBLICATIONS

Bouloc P, Repoila F. 2016. Fresh layers of RNA-mediated regulation in Gram-positive bacteria. Current Opinion in Microbiology 30:30-35.
Brantl S, Brückner R. 2014. Small regulatory RNAs from low-GC Gram-positive bacteria. RNA Biology 11(5):443-456.
Bruder MR, Pyne ME, Moo-Young M, Chung DA, Chou CP. 2016. Extending CRISPR-Cas9 Technology from Genome Editing to Transcriptional Engineering in the Genus *Clostridium*. Applied and Environmental Microbiology 82(20):6109-6119.
Caillet J, Gracia C, Fontaine F, Hajnsdorf E. 2014. Clostridium difficile Hfq can replace *Escherichia coli* Hfq for most of its function. Rna 20(10):1567-78.
Cayrol B, Fortas E, Martret C, Cech G, Kloska A, Caulet S, Barbet M, Trepout S, Marco S, Taghbalout A and others. 2015. Riboregulation of the bacterial actin-homolog MreB by DsrA small noncoding RNA. Integrative Biology 7(1):128-141.
Chang, A. C., and Cohen, S. N. (1978) Construction and characterization of amplifiable multicopy DNA cloning vehicles derived from the P15A cryptic miniplasmid, J. Bacteriol. 134, 1141-1156.
Chen Y, Indurthi DC, Jones SW, Papoutsakis ET. 2011. Small RNAs in the Genus *Clostridium*. mBio 2(1):e00340-10.
Cho, C., & Lee, S. Y. (2017). Efficient gene knockdown in Clostridium acetobutylicum by synthetic small regulatory RNAs. Biotechnology and bioengineering, 114(2), 374-383.
Cho SH, Haning K, Contreras LM. 2015. Strain engineering via regulatory noncoding RNAs: not a one-blueprint-fits-all. Current Opinion in Chemical Engineering 10:25-34.
De Almeida Ribeiro E, Beich-Frandsen M, Konarev PV, Shang W, Večerek B, Kontaxis G, Hämmerle H, Peterlik H, Svergun DI, Bläsi U and others. 2012. Structural flexibility of RNA as molecular basis for Hfq chaperone function. Nucleic Acids Research 40(16):8072-8084.
De Lay N, Schu DJ, Gottesman S. 2013. Bacterial Small RNA-based Negative Regulation: Hfq and Its Accomplices. Journal of Biological Chemistry 288(12):7996-8003.
Dendooven et al. RNA search engines empower the bacterial intranet. Biochemical Society Transactions, vol. 45, pp. 987-997, Jul. 14, 2017. (Year: 2017).
Fender, A., Elf, J., Hampel, K., Zimmermann, B., and Wagner, E. G. H. (2010) RNAs actively cycle on the Sm-like protein Hfq, Genes Dev. 24, 2621-2626.
Fong BA, Wood DW. 2010. Expression and purification of ELP-intein-tagged target proteins in high cell density *E. coli* fermentation. Microb Cell Fact 9:77.
Girbal L, Soucaille P. 1994. Regulation of Clostridium acetobutylicum metabolism as revealed by mixed-substrate steady-state continuous cultures: role of NADH/NAD ratio and ATP pool. Journal of Bacteriology 176(21):6433-6438.
Glascock, C. B., and Weickert, M. J. (1998) Using chromosomal lacIQ1 to control expression of genes on high-copy-number plasmids in *Escherichia coli*, Gene 223, 221-231.
Gottesman S, Storz G. 2010. Bacterial Small RNA Regulators: Versatile Roles and Rapidly Evolving Variations. Cold Spring Harbor Perspectives in Biology.
Gowrishankar, J. (1985) Identification of osmoresponsive genes in *Escherichia coli*: evidence for participation of potassium and proline transport systems in osmoregulation, J. Bacteriol. 164, 434-445.
Green AA, Silver PA, Collins JJ, Yin P. 2014. Toehold switches: de-novo-designed regulators of gene expression. Cell 159(4):925-39.
Green EM, Boynton ZL, Harris LM, Rudolph FB, Papoutsakis ET, Bennett GN. 1996. Genetic manipulation of acid formation pathways by gene inactivation in Clostridium acetobutylicum ATCC 824. Microbiology 142(8):2079-2086.
Guzman, L. M., Belin, D., Carson, M. J., and Beckwith, J. (1995) Tight regulation, modulation, and high-level expression by vectors containing the arabinose PBAD promoter, J. Bacteriol. 177, 4121-4130.

Hao Y, Zhang ZJ, Erickson DW, Huang M, Huang Y, Li J, Hwa T, Shi H. 2011. Quantifying the sequence-function relation in gene silencing by bacterial small RNAs. Proceedings of the National Academy of Sciences, USA 108(30):12473-12478.
Hussein R, Lim HN. 2011. Disruption of small RNA signaling caused by competition for Hfq. Proceedings of the National Academy of Sciences, USA 108(3):1110-1115.
Hussein R, Lim HN. 2012. Direct comparison of small RNA and transcription factor signaling. Nucleic Acids Res 40(15):7269-79.
Ishikawa H, Otaka H, Maki K, Morita T, Aiba H. 2012. The functional Hfq-binding module of bacterial sRNAs consists of a double or single hairpin preceded by a U-rich sequence and followed by a 3' poly(U) tail. Rna 18(5):1062-74.
Jang Y-S, Lee JY, Lee J, Park JH, Im JA, Eom M-H, Lee J, Lee S-H, Song H, Cho J-H and others. 2012. Enhanced Butanol Production Obtained by Reinforcing the Direct Butanol-Forming Route in Clostridium acetobutylicum. mBio 3(5): e00314-12.
Kang Z, Wang X, Li Y, Wang Q, Qi Q. 2012. Small RNA RyhB as a potential tool used for metabolic engineering in *Escherichia coli*. Biotechnol Lett 34(3):527-31.
Keasling JD. 2008. Synthetic Biology for Synthetic Chemistry. ACS Chemical Biology 3(1):64-76.
Khlebnikov, A., Skaug, T., and Keasling, J. D. (2002) Modulation of gene expression from the arabinose-inducible araBAD promoter, J. Ind. Microbiol. Biotechnol. 29, 34-37.
Knoshaug EP, Zhang M. 2009. Butanol tolerance in a selection of microorganisms. Appl Biochem Biotechnol 153(1-3):13-20.
Kushwaha M, Rostain W, Prakash S, Duncan JN, Jaramillo A. 2016. Using RNA as Molecular Code for Programming Cellular Function. ACS Synth Biol 5(8):795-809.
Lahiry, A., Stimple, S. D., Wood, D. W., & Lease, R. A. (2017). Retargeting a dual-acting sRNA for multiple mRNA transcript regulation. ACS synthetic biology, 6(4), 648-658.
Lairy, A., Stimple, S.D., Lease, R., and Wood, D.W. "Metabolic engineering with dual-activing small RNA molecule for improved biofuels fermentations." Abstracts of Papers of the American Chemical Society, vol. 251, p. 122, Abstract BIOT 122, Mar. 13, 2016. (Year: 2016).
Lalaouna D, Masse E. 2016. The spectrum of activity of the small RNA DsrA: not so narrow after all. Curr Genet 62(2):261-4.
Lalaouna D, Morissette A, Carrier M-C, Massé E. 2015. DsrA regulatory RNA represses both hns and rbsD mRNAs through distinct mechanisms in *Escherichia coli*. Molecular Microbiology 98(2):357-369.
Lease RA, Belfort M. 2000. A trans-acting RNA as a control switch in *Escherichia coli*: DsrA modulates function by forming alternative structures. Proc Natl Acad Sci U S A 97(18):9919-24.
Lease RA, Cusick ME, Belfort M. 1998. Riboregulation in *Escherichia coli*: DsrA RNA acts by RNA:RNA interactions at multiple loci. Proc Natl Acad Sci U S A 95(21):12456-61.
Lease RA, Smith D, McDonough K, Belfort M. 2004. The small noncoding DsrA RNA is an acid resistance regulator in *Escherichia coli*. J Bacteriol 186(18):6179-85.
Lease RA, Woodson SA. 2004. Cycling of the Sm-like protein Hfq on the DsrA small regulatory RNA. J Mol Biol 344(5):1211-23.
Levine E, Zhang Z, Kuhlman T, Hwa T. 2007. Quantitative Characteristics of Gene Regulation by Small RNA. PLoS Biol 5(9):e229.
Li F, Wang Y, Gong K, Wang Q, Liang Q, Qi Q. 2014. Constitutive expression of RyhB regulates the heme biosynthesis pathway and increases the 5-aminolevulinic acid accumulation in *Escherichia coli*. FEMS Microbiol Lett 350(2):209-15.
Li Q, Chen J, Minton NP, Zhang Y, Wen Z, Liu J, Yang H, Zeng Z, Ren X, Yang J and others. 2016. CRISPR-based genome editing and expression control systems in Clostridium acetobutylicum and Clostridium beijerinckii. Biotechnology Journal 11(7):961-972.
Liu R, Bassalo MC, Zeitoun RI, Gill RT. 2015. Genome scale engineering techniques for metabolic engineering. Metabolic Engineering 32:143-154.
Liu Y, Zhu Y, Li J, Shin HD, Chen RR, Du G, Liu L, Chen J. 2014. Modular pathway engineering of Bacillus subtilis for improved N-acetylglucosamine production. Metab Eng 23:42-52.

(56) References Cited

OTHER PUBLICATIONS

Lutz, R., and Bujard, H. (1997) Independent and tight regulation of transcriptional units in *Escherichia coli* via the LacR/O, the TetR/O and AraC/I1-I2 regulatory elements., Nucleic Acids Res. 25, 1203-1210.

Majdalani N, Cunning C, Sledjeski D, Elliott T, Gottesman S. 1998. DsrA RNA regulates translation of RpoS message by an anti-antisense mechanism, independent of its action as an antisilencer of transcription. Proc Natl Acad Sci U S A 95(21):12462-7.

Mandin P, Gottesman S. 2010. Integrating anaerobic/aerobic sensing and the general stress response through the ArcZ small RNA. EMBO J 29(18):3094-107.

Masse E, Escorcia FE, Gottesman S. 2003. Coupled degradation of a small regulatory RNA and its mRNA targets in *Escherichia coli*. Genes Dev 17(19):2374-83.

McCullen CA, Benhammou JN, Majdalani N, Gottesman S. 2010. Mechanism of Positive Regulation by DsrA and RprA Small Noncoding RNAs: Pairing Increases Translation and Protects rpoS mRNA from Degradation. J Bacteriol 192(21):5559-5571.

Mitarai N, Benjamin JA, Krishna S, Semsey S, Csiszovszki Z, Masse E, Sneppen K. 2009. Dynamic features of gene expression control by small regulatory RNAs. Proc Natl Acad Sci U S A 106(26):10655-9.

Morgan-Kiss, R. M., Wadler, C., and Cronan, J. E., Jr. (2002) Long-term and homogeneous regulation of the *Escherichia coli* araBAD promoter by use of a lactose transporter of relaxed specificity, Proc. Natl. Acad. Sci. U. S. A. 99, 7373-7377.

Na D, Yoo SM, Chung H, Park H, Park JH, Lee SY. 2013. Metabolic engineering of *Escherichia coli* using synthetic small regulatory RNAs. Nat Biotechnol 31(2):170-4.

Nakayama S-i, Kosaka T, Hirakawa H, Matsuura K, Yoshino S, Furukawa K. 2008. Metabolic engineering for solvent productivity by downregulation of the hydrogenase gene cluster hupCBA in Clostridium saccharoperbutylacetonicum strain N1-4. Applied Microbiology and Biotechnology 78(3):483-493.

Nguyen, A. W., and Daugherty, P. S. (2005) Evolutionary optimization of fluorescent proteins for intracellular FRET, Nat. Biotechnol. 23, 355-360.

Nielsen LK. 2011. Metabolic engineering: From retrofitting to green field. Nat Chem Biol 7(7):408-409.

Panja S, Santiago-Frangos A, Schu DJ, Gottesman S, Woodson SA. 2015. Acidic Residues in the Hfq Chaperone Increase the Selectivity of sRNA Binding and Annealing. Journal of Molecular Biology 427(22):3491-3500.

Park H, Bak G, Kim SC, Lee Y. 2013. Exploring sRNA-mediated gene silencing mechanisms using artificial small RNAs derived from a natural RNA scaffold in *Escherichia coli*. Nucleic Acids Res 41(6):3787-804.

Peer A, Margalit H. 2011. Accessibility and Evolutionary Conservation Mark Bacterial Small-RNA Target-Binding Regions. Journal of Bacteriology 193(7):1690-1701.

Peters G, Coussement P, Maertens J, Lammertyn J, De Mey M. 2015. Putting RNA to work: Translating RNA fundamentals into biotechnological engineering practice. Biotechnol Adv 33(8):1829-44.

Sakai Y, Abe K, Nakashima S, Yoshida W, Ferri S, Sode K, Ikebukuro K. 2014. Improving the Gene-Regulation Ability of Small RNAs by Scaffold Engineering in *Escherichia coli*. ACS Synthetic Biology 3(3):152-162.

Schmiedel JM, Axmann IM, Legewie S. 2012. Multi-Target Regulation by Small RNAs Synchronizes Gene Expression Thresholds and May Enhance Ultrasensitive Behavior. PLoS One 7(8):e42296.

Schollmeier, K., Gärtner, D., and Hillen, W. (1985) A bidirectionally active signal for termination of transcription is located between tetA and orfL on transposon Tn10, Nucleic Acids Res. 13, 4227-4237.

Schu DJ, Zhang A, Gottesman S, Storz G. 2015. Alternative Hfq-sRNA interaction modes dictate alternative mRNA recognition. Embo j 34(20):2557-73.

Sharma V, Yamamura A, Yokobayashi Y. 2012. Engineering Artificial Small RNAs for Conditional Gene Silencing in *Escherichia coli*. ACS Synthetic Biology 1(1):6-13.

Shi, X., and Bennett, G. N. (1994) Plasmids bearing hfq and the hns-like gene stpA complement hns mutants in modulating arginine decarboxylase gene expression in *Escherichia coli*, J. Bacteriol. 176, 6769-6775.

Sledjeski DD, Gupta A, Gottesman S. 1996. The small RNA, DsrA, is essential for the low temperature expression of RpoS during exponential growth in *Escherichia coli*. Embo J 15(15):3993-4000.

Sledjeski, D. D., Whitman, C., and Zhang, A. (2001) Hfq is necessary for regulation by the untranslated RNA DsrA, J. Bacteriol. 183, 1997-2005.

Stimple et al. Chapter 21. Veronique Arlusion and Claudio Valverde (eds.) Bacterial Regulatory RNA: Methods and Protocols, Methods in Molecular Biology, vol. 1737, Springer Science+Business Media, LLC 2018. (Year: 2018).

Storz G, Vogel J, Wassarman KM. 2011. Regulation by small RNAs in bacteria: expanding frontiers. Mol Cell 43(6):880-91.

Tashiro Y, Shinto H, Hayashi M, Baba S-i, Kobayashi G, Sonomoto K. 2007. Novel high-efficient butanol production from butyrate by non-growing Clostridium saccharoperbutylacetonicum N1-4 (ATCC 13564) with methyl viologen. Journal of Bioscience and Bioengineering 104(3):238-240.

Timmes, A., Rodgers, M., and Schleif, R. (2004) Biochemical and physiological properties of the DNA binding domain of AraC protein, J. Mol. Biol. 340, 731-738.

Tummala SB, Junne SG, Papoutsakis ET. 2003. Antisense RNA Downregulation of Coenzyme A Transferase Combined with Alcohol-Aldehyde Dehydrogenase Overexpression Leads to Predominantly Alcohologenic Clostridium acetobutylicum Fermentations. J. Bacteriol. 185(12):3644-3653.

Updegrove TB, Zhang A, Storz G. 2016. Hfq: the flexible RNA matchmaker. Current Opinion in Microbiology 30:133-138.

Urban JH, Vogel J. 2007. Translational control and target recognition by *Escherichia coli* small RNAs in vivo. Nucleic Acids Res 35(3):1018-37.

Urban et al. "A Green Fluorescent Protein (GFP)-Based Plasmid System to Study Post-Transcriptional Control of Gene Expression In Vivo." Alexander Serganov (ed.), Riboswitches, Methods in Molecular Biology, vol. 540, Humana Press, a part of Springer Science+Buisness Media, LLC 2009, pp. 301-319. (Year: 2009).

Vazquez-Anderson J, Contreras LM. 2013. Regulatory RNAs: Charming gene management styles for synthetic biology applications. RNA Biology 10(12):1778-1797.

Vellanoweth, R. L., and Rabinowitz, J. C. (1992) The influence of ribosome-binding-site elements on translational efficiency in Bacillus subtilis and *Escherichia coli* in vivo, Mol. Microbiol. 6, 1105-1114.

Venkataramanan K, Jones S, McCormick K, Kunjeti S, Ralston M, Meyers B, Papoutsakis E. 2013. The Clostridium small RNome that responds to stress: the paradigm and importance of toxic metabolite stress in C. acetobutylicum. BMC Genomics 14(1):849.

Vick, J. E., Johnson, E. T., Choudhary, S., Bloch, S. E., Lopez-Gallego, F., Srivastava, P., Tikh, I. B., Wawrzyn, G. T., and Schmidt-Dannert, C. (2011) Optimized compatible set of BioBrick™ vectors for metabolic pathway engineering, Appl. Microbiol. Biotechnol. 92, 1275-1286.

Vogel, J., and Luisi, B. F. (2011) Hfq and its constellation of RNA, Nat Rev Micro 9, 578-589.

Wagner EG, Romby P. 2015. Small RNAs in bacteria and archaea: who they are, what they do, and how they do it. Adv Genet 90:133-208.

Wang JS, Zhang DY. 2015. Simulation-guided DNA probe design for consistently ultraspecific hybridization. Nat Chem 7(7):545-553.

Yu M, Zhang Y, Tang IC, Yang S-T. 2011. Metabolic engineering of Clostridium tyrobutyricum for n-butanol production. Metabolic Engineering 13(4):373-382.

Zadeh JN, Steenberg CD, Bois JS, Wolfe BR, Pierce MB, Khan AR, Dirks RM, Pierce NA. 2011. NUPACK: Analysis and design of nucleic acid systems. J Comput Chem 32(1):170-3.

Non-Final Office Action issued for U.S. Appl. No. 15/865,983, dated Jul. 6, 2018.

(56) References Cited

OTHER PUBLICATIONS

Non-Final Office Action issued for U.S. Appl. No. 15/865,983, dated Feb. 5, 2019.
Final Office Action issued for U.S. Appl. No. 15/865,983, dated Jul. 23, 2019.
Non-Final Office Action issued for U.S. Appl. No. 15/865,983, dated Feb. 21, 2020.

* cited by examiner

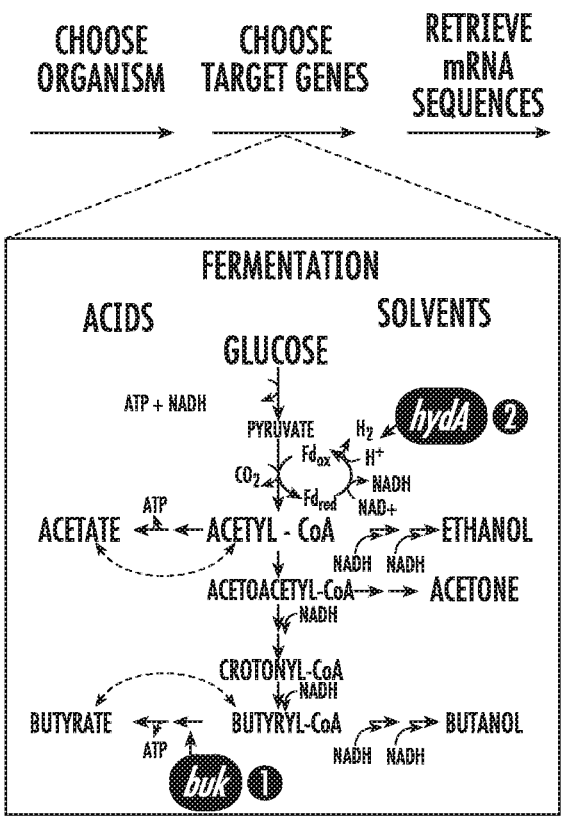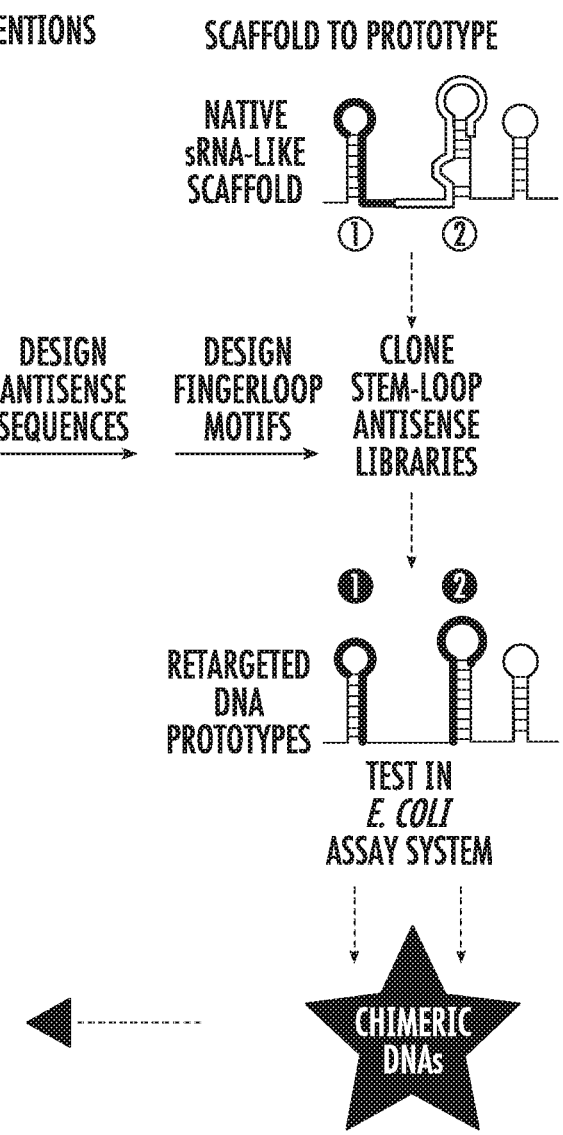
FIG. 3A
FIG. 3B

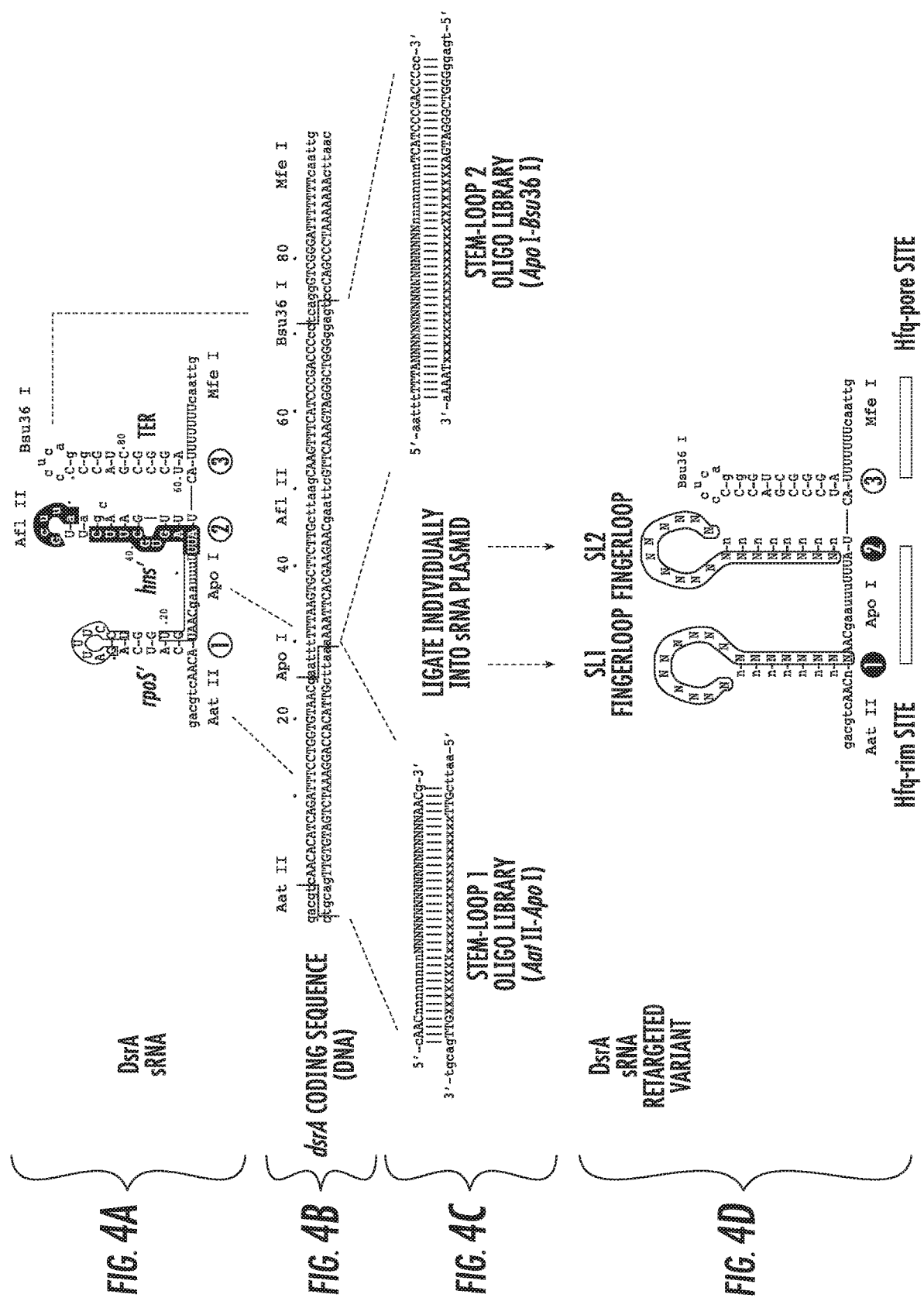

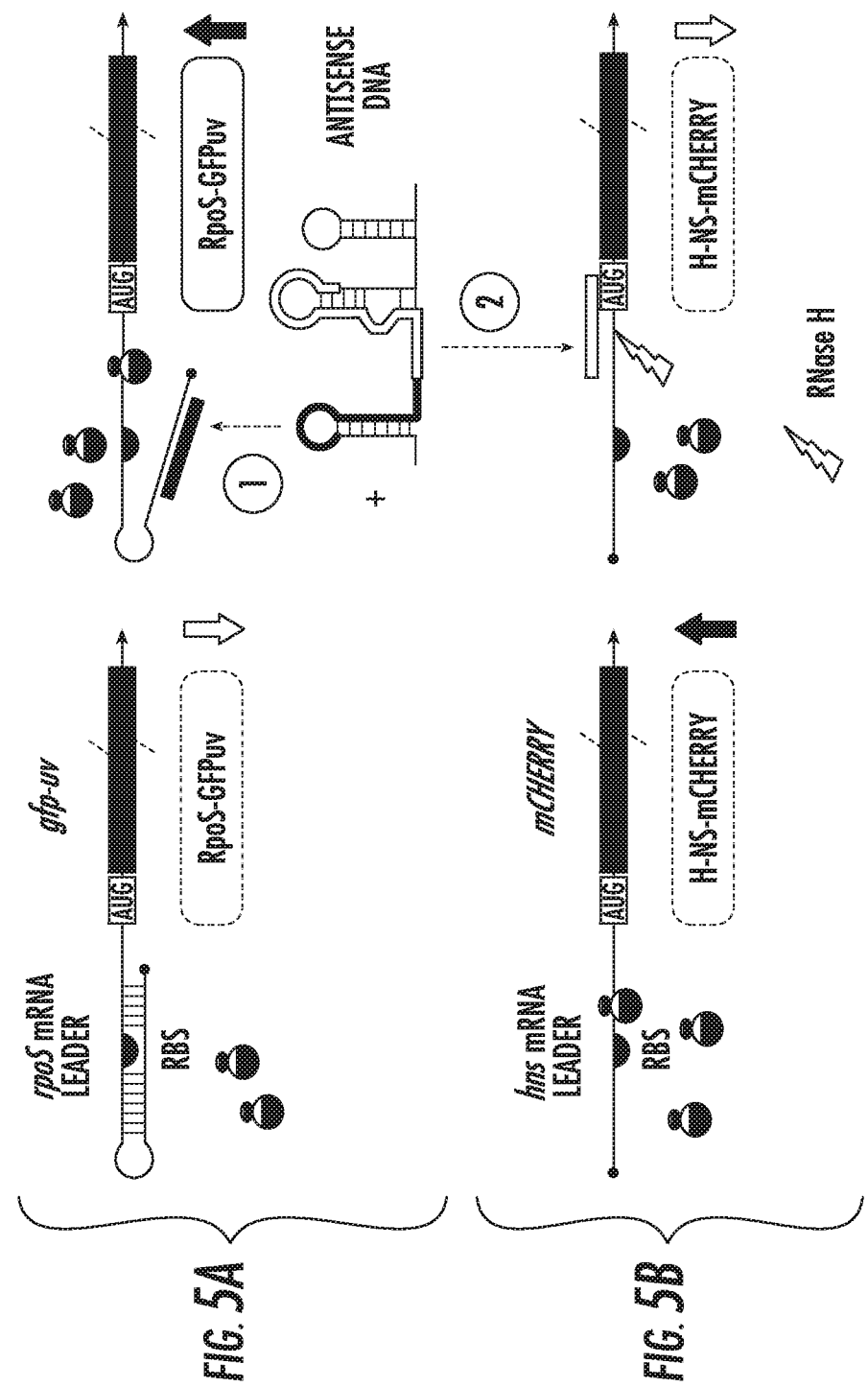

| | mRNA (hydA::mCherry variant) | | | |
|---|---|---|---|---|
| FOLD DECREASE | hydA+ | hydA -5 | hydA -7 | hydA -5,7 |
| L7 | 16.1 | 23.2 | 4.1 | 4.3 |
| L7 (-5) | 19.7 | 13.4 | 7.1 | 8.7 |
| L7 (-7) | 1.8 | 1.2 | 11.9 | 8.5 |
| L7 (-5, -7) | 3.1 | 2.7 | 10.7 | 7.8 | sRNA VARIANT

ANTISENSE BASIS = DsrA-hydA'2.4.1

```
                  DsrA-hydA'(inv)  L7        1111    Stem
                                   7654321210987654321
              3'..UAAAGUACAAAUCCCUCCUAUUUGUACUUUA..5'
                                   |||||||  |||||||||
hydA mRNA  DsrA'-L7        5'..GGGGAGGAUAAACAUGAAA..3'
(-7)       L2/7                   GGGAGCAUAAACAUGAAA              ──┐
(-10)      L2/7                   GGCAGGAUAAACAUGAAA                │  LOOP
(-5,7)     L2+S12                 GGGAGCAaAAACAUGAAA                │  INTERACTION
(-5,10)    L5+S12                 GGCAGGAaAAACAUGAAA                │
(-7,10)    L2+L5                  GGcAGCAAAAACAUGAAA                │
(-5,7,10)  L2,5,12                GGcAGCAaAAACAUGAAA              ──┘
(-5)       S12                    GGGAGGAaAAACAUGAAA
(-4)       S11                    GGGAGGAUaAACAUGAAA
(-1)       S8                     GGGAGGAUAAAgCAUGAAA
(-1,4)     S8+S11                 GGGAGGAUuAAgAUGAAA               ──┐  STEM
(+5)       S8                     GGGAGGAUAAAgAUGACA                │  INTERACTION
(+5,-1)    S3+S8                  GGGAGGAUAAAgAUGACA              ──┘
                                           ++++++
                                  111000000000123456
                                  2109876543211
```

7nt RNA FINGERLOOP
hydA'2.4.1
(as DsrA' STEM LOOP 2)

FIG. 10

ANTISENSE FINGERLOOP DNAS AND USES THEREOF

CROSS REFERENCE TO RELATED APPLICATIONS

This application is a national stage application filed under 35 U.S.C. § 371 of PCT/US2018/042739 filed Jul. 18, 2018, which claims the benefit of U.S. Provisional Patent Application Ser. No. 62/533,857 filed Jul. 18, 2017, and U.S. Provisional Patent Application Ser. No. 62/562,105 filed Sep. 22, 2017, each of which are expressly incorporated herein by reference.

STATEMENT REGARDING FEDERALLY FUNDED RESEARCH

This invention was made with government support under CBET1158394 awarded by the National Science Foundation. The government has certain rights in the invention.

FIELD

The present disclosure relates to improved methods for detecting nucleic acids using DNA fingerloop stem loop structures, wherein the DNA fingerloop stem loop structures diminish base pairing of a detection probe to a mismatched target nucleic acid. The present disclosure also relates to improved methods for amplifying nucleic acids. Further disclosed are chimeric fingerloop DNAs for use in methods for modulating protein expression levels and/or RNA stability.

REFERENCE TO SEQUENCE LISTING

The Sequence Listing submitted Mar. 6, 2022 as a text file named "10336-369US1_2022_04_06_Sequence_Listing.txt," created on Mar. 6, 2022, and having a size of 11,089 bytes is hereby incorporated by reference pursuant to 37 C.F.R. § 1.52(e)(5).

BACKGROUND

The use of DNA in biology applications has enormous potential. There are many different applications in molecular biology that rely on the hybridization of an antisense nucleic acid, for example, molecular beacons, polymerase chain reaction (PCR), as well as additional probes used in Northern and Southern blot analysis. However, one of the drawbacks of these hybridization technologies is the potential for hybridization to mismatched targets (or hybridization to non-target sequences). What is needed are new and improved methods for filtering these mismatched target sequences and improving the detection and amplification of target nucleic acid sequences.

In addition, while RNA tools have been successfully developed for altering gene expression, building genetic circuitry, and for sensing small molecules and other environmental cues, use of DNA tools has been limited. Small non-coding RNAs, such as miRNAs, siRNAs and piRNAs, all about 21-32 nt in length, are one of the main and crucial classes of posttranscriptional gene regulators in eukaryotes. Being expressed under tight spatial and temporal control, small non-coding RNAs influence all aspects of organism's biology, including its development, metabolism and response to environmental conditions.

The importance of another class of small non-coding RNAs, bacterial small regulatory RNAs (sRNAs), became apparent only recently due to ongoing intensive research in prokaryote genetics and genomics. Compared to conventional metabolic engineering approaches such as gene knockouts, the sRNAs of bacteria present the distinct advantage of being able to "tune" gene expression, modulating mRNA translation levels with relatively fine control. However, while RNAs have been explored for tuning gene expression, use of DNA fingerloop stem loop structures and chimeric DNAs remains unexplored.

The systems and methods disclosed herein address these and other needs.

SUMMARY

Disclosed herein are novel methods for the detection and amplification of nucleic acids using DNA fingerloop stem loop structures. The inventors have found that these DNA fingerloop stem loop structures can diminish base pairing of a detection probe to a mismatched target nucleic acid.

In some aspects, disclosed herein is a method for detecting a target nucleic acid sequence, comprising the steps:
providing a nucleic acid sample from a subject;
detecting the target nucleic acid sequence using a detection probe, wherein the detection probe comprises a DNA fingerloop stem loop structure;
wherein the DNA fingerloop stem loop structure comprises an antisense region that binds to the target nucleic acid sequence;
wherein the antisense region is located in a loop and in one strand of the stem loop of the DNA fingerloop stem loop structure; and
wherein the DNA fingerloop stem loop structure diminishes base pairing to a mismatched target nucleic acid.

In some embodiments, the DNA fingerloop stem loop structure provides increased detection specificity of the target nucleic acid sequence.

In some embodiments, the detection probe is a molecular beacon. In some embodiments, the detection probe is a Northern blot probe. In some embodiments, the detection probe is a Southern blot probe.

In some embodiments, the one strand of the stem loop is the descending strand of the stem loop. In some embodiments, the one strand of the stem loop is the ascending strand of the stem loop.

In some embodiments, the antisense region that binds to the target nucleic acid sequence comprises from about 10 to about 35 nucleotides. In some embodiments, the DNA fingerloop stem loop structure that binds to the target nucleic acid sequence comprises from about 25 to about 60 nucleotides.

In some aspects, disclosed herein is a method for amplifying a nucleic acid sequence, comprising the steps:
providing a nucleic acid sample from a subject;
amplifying the nucleic acid sequence using amplification primers in a polymerase chain reaction, wherein the amplification primers comprise a fingerloop stem loop structure;
wherein the DNA fingerloop stem loop structure comprises an antisense region that binds to a region flanking the nucleic acid sequence;
wherein the antisense region is located in a loop and in one strand of the stem loop of the DNA fingerloop stem loop structure; and
wherein the DNA fingerloop stem loop structure diminishes base pairing to a mismatched target nucleic acid.

In some embodiments, the amplification primers comprise from about 25 to about 100 nucleotides. In some embodiments, the antisense region that binds to the target nucleic acid sequence comprises from about 10 to about 35 nucleotides. In some embodiments, the DNA fingerloop stem loop structure that binds to the target nucleic acid sequence comprises from about 25 to about 60 nucleotides.

Further disclosed herein are novel systems and methods to measure the activity of DNA fingerloop stem loop structures and chimeric DNAs in a cell and methods of using these chimeric DNA fingerloop molecules for measuring and modulating protein expression levels and/or RNA stability from multiple mRNAs in a cell simultaneously. These improved methods provide a system for the novel and modular production of chimeric DNA molecules that target multiple mRNAs in a cell simultaneously.

In some aspects, disclosed herein is a method for modulating protein expression levels and/or mRNA expression levels from at least two target mRNAs in a cell simultaneously, the method comprising:
transforming the cell with a system for measuring the activity of a chimeric deoxyribonucleic acid (DNA), the system comprising:
a chimeric DNA, wherein the chimeric DNA comprises a first deoxyribonucleic acid (DNA) sequence operably linked to a second deoxyribonucleic acid (DNA) sequence;
a first plasmid comprising a first reporter gene operably linked to a first gene leader sequence; and
a second plasmid comprising a second reporter gene operably linked to a second gene leader sequence;
wherein the first DNA sequence is present in a first stem loop and the second DNA sequence is present in a second stem loop;
wherein the first and second stem loops inhibit the binding of the first and second DNAs to mismatched target sequences;
wherein the first DNA sequence binds to an mRNA of the first gene leader sequence and the second DNA sequence binds to an mRNA of the second gene leader sequence; and
measuring the protein expression levels and/or mRNA expression levels of the first reporter gene and the second reporter gene.

In some embodiments, the DNA fingerloop stem loop structure comprises an antisense region that binds to a region flanking the nucleic acid sequence; and/or the antisense region is located in a loop and in one strand of the stem loop of the DNA fingerloop stem loop structure; and/or the DNA fingerloop stem loop structure diminishes base pairing to a mismatched target nucleic acid.

In some embodiments, the first DNA sequence and the second DNA sequence are comprised in at least two stem loop structures.

In some embodiments, the first DNA sequence binds to an mRNA of the first gene leader sequence. In some embodiments, the second DNA sequence binds to an mRNA of the second gene leader sequence.

In some embodiments, the first reporter gene encodes a fluorescent protein. In some embodiments, the second reporter gene encodes a fluorescent protein. In some embodiments, the chimeric DNA is from about 50 to about 300 nucleotides in length.

In some embodiments, the cell is an *Escherichia coli* cell. In some embodiments, the cell is a *Clostridium acetobutylicum* cell. In some embodiments, the cell is a *Bacillus subtilis* cell.

In some embodiments, the chimeric DNA binds to the at least two target mRNAs encoding at least two cell enzymes, and wherein binding results in a reduction of activity of the at least two cell enzymes.

In some embodiments, the at least two target mRNAs are in the same metabolic pathway. In some embodiments, the at least two target mRNAs are in different metabolic pathways.

BRIEF DESCRIPTION OF THE DRAWINGS

The accompanying figures, which are incorporated in and constitute a part of this specification, illustrate several aspects described below.

FIGS. 3A-3B. Prototyping dual-acting targeted chimeric DNAs in vivo. To coordinate two simultaneous interventions in a metabolic pathway, a retargeting system was created for assaying dual-acting sRNA. The system is amenable for similar interventions for optimizing DNA as a regulatory tool in vivo. (FIG. 3A) A particular metabolic engineering intervention will inform the choice of two target mRNAs to be tuned by coordinate regulation (e.g., improved n-butanol fermentation selectivity and yield; buk and hydA mRNAs of *Clostridium acetobutylicum*) using a retargeted chimeric DNA (right). (FIG. 3B) Retargeted antisense DNA "fingerloop" library variants, based on the DsrA sRNA scaffold structure, are designed to pair with these mRNA targets. The mRNAs to be tested are prepared as fusions with two fluorescent reporter genes, and effects of chimeric DNA variants are quantified during expression in E. coli. Successful prototype chimeric DNAs could then be introduced into a desired host organism, ideally without modification of the host genome.

FIGS. 4A-4D. Modular cloning of chimeric DNA antisense domains. (FIG. 4A) The secondary structure model of DsrA in the sRNA plasmid context, with the location of corresponding restriction sites highlighted in red. The use of restriction sites Aat II and Apo I, or Apo I and Bsu36 I, for cloning permit modular exchange of stem-loops 1 or 2, respectively. (FIG. 4B) The dsrA DNA gene sequence with cleavage patterns in Aat II, Apo I and Bsu36 I superimposed on the restriction sites (lowercase letters). Pairs of annealed DNA oligonucleotides can thus be designed to create compatible ends that introduce synthetic fingerloops or unstructured antisense regions as desired. Uppercase N (in cyan) represents the 18-mer antisense sequence that targets a transcript; lowercase n (cyan) represents the sequence used to compete the fingerloop structure; lowercase and uppercase X sequences encode complementary Watson-Crick base pairs in the opposite oligo strand. This process creates modular dsDNA structured antisense fragments to be ligated for creation of fingerloops as a chimeric DNA expressed from a retron or similar reverse transcriptase-based genetic element in vivo. (FIG. 4C) The orientation of fingerloops in a DsrA derivative structure that mimics the DsrA native structure. (FIG. 4D) Mismatches can be engineered into stems by altering single "n" nucleotides to perturb stem stability. The lengths of loop and stem sequences can also be changed to vary regulatory outcomes. The sequence found in FIG. 4A are gacgtcAACACAUCAGAUUCCUGGU-GUAACgaauuuUUUAAGUGCUUCUUGcuuaagc AAGUUUCAUCCCGACCCccucaggGUCGG-GAUUUUUUUcaattg (SEQ ID NO: 7). The sequence found in FIG. 4B are gacgtcAACACATCAGAT-TTCCTGGTGTAACgaatttTTTAAGTGCTTCTTGct-taagCAAGT TTCATCCCGACCCcctcaggGTCGGGAT-TTTTTTcaattgctgcagTTGTGTAGTCTAAAGGA CCACATTGcttaaaAAATTCACGAAGAAGAACgaat-tcGTTCAAAGTAGGGCTGGGggagt ccCAGCCCTAAAAAAActtaac (SEQ ID NO: 8). The sequences found in FIG. 4C are cAACnnnnnnnnNNNNNNNNNNNNNNNNNNNNAACg (SEQ ID NO: 9), aat-tcGTTxxxxxxxxxxxxxxxxxxXXXXXXXXGTTgacgt (SEQ ID NO: 10), aatttTT-TANNNNNNNNNNNNNNNNNNNnnnnnnnnT-CATCCCGACCCcc (SEQ ID NO:11), and tgaggGGGTCGGGAT-GAXXXXXXXXxxxxxxxxxxxxxxxxxxTAAAa (SEQ ID NO: 12). The sequences in FIG. 4D are gacgt-cAACnnnnnnnnNNNNNNNNNNNNNNNNN-NAACgaauuuUUUANNNNNNNNNN NNNNNNNnnnnnnnnUCAUCCCGACCCccucaggGU-CGGGAUUUUUUUcaattg (SEQ ID NO: 13).

FIGS. 5A-5B. Reporter gene system for analysis of chimeric DNA acting simultaneously at two target mRNA sequences. Alteration of mRNA levels is manifest in the cell as individually altered fluorescent protein levels (by altered protein translation). (FIG. 5A) The chimeric antisense DNA activates an intrinsically repressed rpoS transcript reporter fusion (above left, green); RpoS-GFPuv is off-by-default unless activated by the chimeric DNA. (FIG. 5B) The chimeric antisense DNA enhances the turnover of has transcript fusions (below left, red). H-NS-mCherry is on-by-default unless deactivated by chimeric DNA antisense mechanism. Black dome represents ribosome binding site. Gray paired circles represent ribosomes. Circled numbers indicate chimeric DNA:mRNA interactions via individual fingerloop stem-loop structures 1 and 2. Lightning represents a RNA target elimination by RNase H which degrades the RNA portion of RNA:DNA hybrids.

FIG. 4). The native-like fingerloop structure of DsrA stem loops was conserved while using larger loop regions. Boxed sequences in stem-loop 1 (panel a, middle) or stem-loop 2 (panel b, middle) indicate the location of synthetic antisense sequences in the stem-loop structure (gray uppercase "N" residues). Base pairs (black lowercase "n" residues) were added to maintain a stem-loop of approximately the same stability in the same location as wild-type DsrA structure. In some cases, mismatches can be introduced into a stem sequence to optimize the helix stability relative to a desired target. (A) Anti-sense sequences targeting the TIR of gene 1 (buk, above) were cloned to replace chimeric DNA stem-loop 1 with a synthetic fingerloop motif (b) Anti-sense sequences targeting the TIR of gene 2 (hydA, below) were similarly cloned to replace chimeric DNA stem-loop 2. A series of antisense sequence "tiles" were designed to pair with the TIR sequences of target mRNAs and are used to prepare a small anti-sense fingerloop DNA library for each target (horizontal black bars). Each library of chimeric DNA variants contains sequences that are antisense to the new target mRNA translation initiation region (TIR), starting at the ribosome-binding site (RBS) region of the TIR-reporter fusion construct. The sequences found in FIG. 7A are gacgtcAACAnnnnnnnnNNNNNNNNNNNNNNNNN-NAACgaatttTTTAAGTGCTTCTTGctta agcAAGTTT-CATCCCGACCCcctcaggGTCGGGATTTTTTTcaattg (SEQ ID NO: 14). The sequences found in FIG. 7B are gacgtcAACACATCAGATTTCCTGGTGTAACgaatttTT-TANNNNNNNNNNNNNNNNNN nnnnnnnnT-CATCCCGACCCcctcaggGTCGGGATTTTTTTcaattg (SEQ ID NO: 15).

(FIG. 8A) Location of mismatches in the fingerloop and target structures that were tested as compensatory mutants in a mutated reporter gene series (also see FIG.

1, FIG. 12). (FIG. 8B) Heat map of fold-effect regulation. Pure white squares represent active sRNA that tunes down mCherry reporter gene expression. Pure red squares represent strongly decreased activity by sRNA variants at the reporter gene construct. For example, the sRNA L7 (7-membered loop) has 16-fold repression of the wild type hydA+ reporter gene (upper left square, pink) but a mutation in the fingerloop loop region (L7(-7)) loses activity (1.8-fold repression, first column, third row, red). The observed behavior is consistent with both restoration of function in matching mutant pairs, but also with loss of function by mutations on either strand that disrupt pairing in the fingerloop loop. Reporter gene mutations corresponding to the stem region of the fingerloop (top row, reporter hydA-5) are better-tolerated than those corresponding to the fingerloop loop (top row, compare reporter hydA-5 to hydA-7 using the L7 fingerloop; 23-fold repression activity for the stem-pairing nucleotide, decreased to 4-fold repression activity for the loop-pairing nucleotide). The sequences found in FIG. 8A are AUUUCAUGUUUAuUCgCUCCCuaaacaugaaaU (SEQ ID NO: 16) and uuuacauuuuGGGcAGG-cAuaauaacgAUGaaaacaauaaucuua (SEQ ID NO:17).

FIG. 10. Design of a series of hydA-mCherry mutant variants for testing mismatch filtering. The DsrA-hydA RNA:RNA complex is depicted above with DsrA in the inverse (3-5') orientation. Loop nucleotides are in green, stem nucleotides are in black, labeled above. A series of mismatches were engineered into the hydA portion of the hydA-mCherry fluorescent reporter gene (central panel). These mutations correspond to different locations in the antisense loop (shown right; antisense sequence in loop is in white letters on a black background). The numbering of hydA nucleotides is based on their location relative to the +1 AUG start codon (below main panel, blue letters for −1 to −12; black letters for +1 to +6). The numbering system in the fingerloop is given as L (loop position) 1-7 or as S (stem position) 1-12. Both numbering systems are to the left of the panel of mutations (red, underlined) in the hydA reporter gene fusion, and are also depicted in red next to the fingerloop. The sequences found in FIG. 10 are AUUU-CAUGUUUAUCCUCCCUAAACAUGAAAU (SEQ ID NO: 18), GGGAGGAUAAACAUGAAAGGGAG-cAUAAACAUGAAAGGcAGGAUAAACAUGAA AGG-GAGcAaAAACAUGAAAGGcAGGAaAAA-CAUGAAAGGcAGcAUAAACAUGAA AGGcAGcAaAAACAUGAAAGGGAGGAaAAA-CAUGAAAGGGAGGAUuAACAUGAA AGGGAG-GAUAAAgAUGAAAGGGAGGAUuAAgAUGAAAGG-GAGGAUAAAcAUGA cAGGGAGGAUAAAgAUGAcA, (SEQ ID NO: 19), and UAUUUCAUGUUUAUCCUCCC-uaaacaugaaaU (SEQ ID NO: 20).

(FIG. 11A) Small library of reporter gene mutations in TIR. Signal is on by default, reduced by sRNA activity. (FIG. 11B) Panel of reporter gene mutants. (FIG. 11C) Unstructured (ΔS8) sRNA variant is active against mutant reporter gene constructs without much bias. (FIG. 11D) Fingerloop structured antisense filters mismatches in the loop, but not the stem, providing a basis of off-target mRNA filtering. The sequences found in FIG. 11A are AUUUCAUGUUUAUCCUCCCU (SEQ ID NO.: 21) and uuuacauuuuGGGcAGGcAuaauaacgAUGaaaacaauaaucuua (SEQ ID NO: 22). The sequences found in FIG. 11C are AUUUCAUGUUUAUCCUCCCuaaacaugaaaU (SEQ ID NO: 23) and uuuacauuuuGGGcAGG-cAuaauaacgAUGaaaacaauaaucuua (SEQ ID NO: 24).

(FIG. 14A) The antisense sequence was conserved whereas additional sequence (cyan) was added to the base of the stem to increase stem stability. (FIG. 14B) The loop size was varied by adding nucleotides on the opposing strand (cyan), even as the stem stability was made roughly equivalent by alteration of stem sequences on the opposite side of the helix (red arrows to red nucleotides). (FIG. 14C) Assay of stem series depicted in (A). (FIG. 14D) Assay of loop series depicted in (B). A pink (X) indicates compromised function of indicated fingerloop structures. In summary, the minimal functional loop size is 3 nt when stem contributions are isolated as a variable. Loop efficacy scales with loop size up to 5-6 nt. Thus, stem free energy is not the sole determinant of fingerloop efficacy, as −18 kcal/mole L7 represses, but −18 kcal/mole L3 is compromised for function. There may be a limit of ~−20 kcal/mole for a functional 18-mer antisense-sequence fingerloop. The balance of sRNA, mRNA and sRNA:mRNA complex stabilities are probably critical to the formation of RNA:RNA interactions. The sequences found in FIG. 14A are UAugaacacUUU-CAUGUUUAUCCUCCCuaaacaugaaaguguucac (SEQ ID NO: 25), UAgaacacUUUCAUGUUUAUCCUCCCuaaa-caugaaaguguucc (SEQ ID NO: 26), UAaacacUUUCAU-GUUUAUCCUCCCuaaacaugaaaguguuc (SEQ ID NO: 27), UAacacUUUCAUGUUUAUCCUCCCuaaacaugaaaguguc (SEQ ID NO: 28), UAcacUUUCAUGUUUAUCCUCCC-uaaacaugaaagugc (SEQ ID NO:29), UAacUUUCAU-GUUUAUCCUCCCuaaacaugaaaguc (SEQ ID NO:30), and UAcUUUCAUGUUUAUCCUCCCuaaacaugaaagc (SEQ ID NO:31). The sequences found in FIG. 14B are UAUUU-CAUGUUUAUCCUCCCauaaacaugGaGU (SEQ ID NO: 32), UAUUUCAUGUUUAuccuCCCgaugaauauggagU (SEQ ID NO: 33), UAUUUCAUGUUUAUccucccg-gaugaaugauggagU (SEQ ID NO: 34), UAUUUCAU-GUUUAUccUCCCagggugaaugauggaaU (SEQ ID NO: 35), and UAUUUCAUGUUUAUccUcccugaggauugaaugaug-gaaU (SEQ ID NO: 36).

(FIG. 15A) Compared to the original 18-mer, variants of 19-23 nucleotides of antisense sequence were synthesized to test their capacity to pair with a mismatched target. Extra antisense sequence at the 5'-end is shown in yellow. (FIG. 15B) The equivalent sequences configured as a DNA fingerloop oligo. The anticipated pairing to wild-type hydA and the anticipated exclusion of the hydA-7 target DNA are also shown. (FIG. 15C) Antisense fingerloops of 18-23 nucleotides are depicted as structural cartoon drawings with the anticipated base parings. Loop sizes remain 7 nucleotides, stems are constant length, but the antisense content of the stem sequence increases by one nucleotide for each additional construct (going left to right; see arrow and plus symbols for added nucleotides in yellow). The predicted free energies of these species are shown to vary only over a narrow range (below; prediction by NuPack analysis). The sequences found in FIG. 15A are TTTCATGTT-TATCCTCCC (SEQ ID NO: 37), ATTGTTTTCATGTT-TATCCTCCC (SEQ ID NO: 38), ATTTTGGgaggataaacAT-GaaaacaataatcttagcTAGCCGTA (SEQ ID NO: 39), and ATTTTGGgagcataaacATGaaaacaataatcttagcTAGCCGTA (SEQ ID NO: 40). The sequences found in FIG. 15B are ATTGTTTTCATGTTTATCCTCCCtaaacatgaaaacaat (SEQ ID NO: 41), ATTTTGGgaggataaacATGaaaacaataatct-tagcTAGCCGTA (SEQ ID NO:42), and ATTTTGGgagcat-aaacATGaaaacaataatcttagcTAGCCGTA (SEQ ID NO: 43). The sequences found in FIG. 15C are tacacTTTCATGTT-TATCCTCCCtaaacatgaaagtgta (SEQ ID NO: 44), tacaT-TTTCATGTTTATCCTCCCtaaacatgaaaatgta (SEQ ID NO: 45), tacGTTTTCATGTTTATCCTCCCtaaacatgaaaacgta (SEQ ID NO: 46), taTGTTTTCATGTTTATCCTCCCtaaa-catgaaaacata (SEQ ID NO: 47), tTTGTTTTCATGTT-TATCCTCCCtaaacatgaaaacaaa (SEQ ID NO: 48), and ATTGTTTTCATGTTTATCCTCCCtaaacatgaaaacaat (SEQ ID NO: 49).

DETAILED DESCRIPTION

Figure 1:
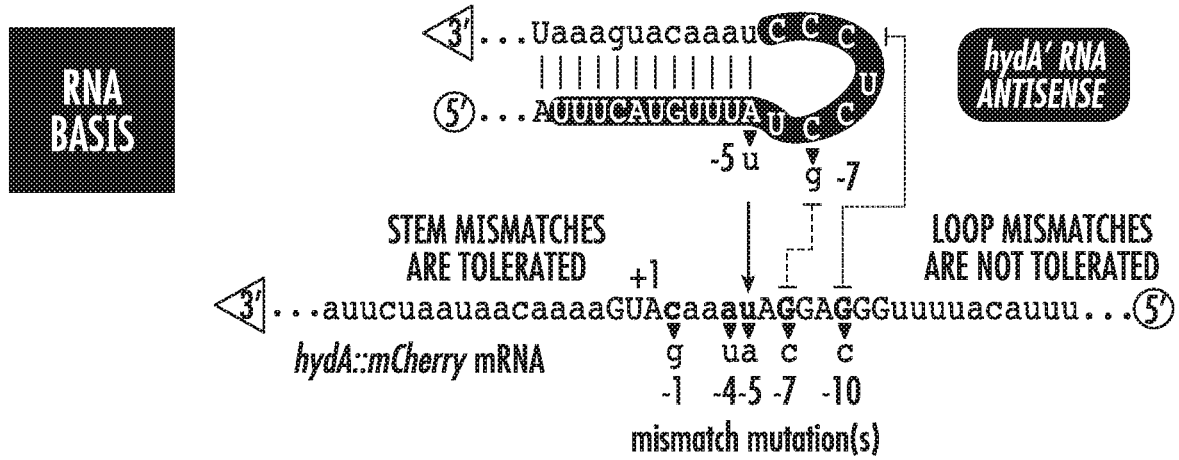
FIG. 1. Overview of fingerloop RNA structure and the phenomenon of mismatch exclusion activity (hybridization filtering). Above, a stem-loop or hairpin RNA helix (vertical lines indicate base pairs between RNA nucleotides A, U, G, C). The reverse-contrast highlighted portion is an "antisense" sequence of RNA that is complementary to a target mRNA species (below), specifically *Clostridium acetobutylicum* hydA mRNA leader region (+1 is the start codon, strand is in reverse order for presentation). The 5' ends are marked with a circle and the 3'-ends are marked with a triangle. The location of the antisense sequence in the stem-loop is distinguishing and is called a Fingerloop. Base pairing between the loop region and the target is a seed/nucleating event which results in duplex formation between the loop antisense sequence and the target (sense) sequence. Mismatches between the two species that require pairing in the loop are excluded from pairing, and the formation of the duplex is blocked. The sequences found in FIG. 1 are AUUUCAUGUUUAUCCUCCCuaaacaugaaaU (SEQ ID NO: 1) and uuuacauuuuGGGcAGGcAuaauaacgAUGaaaacaauaaucuua (SEQ ID NO: 2).

Disclosed herein are novel methods for the detection and amplification of nucleic acids using DNA fingerloop stem loop structures. The inventors have found that these DNA fingerloop stem loop structures can diminish base pairing of a detection probe to a mismatched target nucleic acid. Also disclosed herein are novel systems and methods to measure the activity of chimeric DNAs in a cell and methods of using these chimeric DNA molecules for measuring and modulating protein expression levels and/or RNA stability from multiple mRNAs in a cell simultaneously. Based on the naturally occurring small regulatory RNAs seen in bacteria, the inventors have determined that chimeric DNA molecules, when present in fingerloop stem loop structures, were able to diminish base pairing from mismatched targets. These improved methods provide a system for the novel and modular production of DNA fingerloop stem lop structures and chimeric DNA molecules that target multiple mRNAs in a cell simultaneously.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

As used herein, the article "a," "an," and "the" means "at least one," unless the context in which the article is used clearly indicates otherwise.

As used herein, the phrase "and/or" indicates that any one or any combination of a list of options can be used. For example, "A, B, and/or C" means "A", or "B", or "C", or "A and B", or "A and C", or "B and C", or "A and B and C".

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 150 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), translation initiation regions (TIRs), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the (β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e., a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequent coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength of 3, an expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

Nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in the same reading frame. However, operably linked nucleic acids (e.g. enhancers and coding sequences) do not have to be contiguous. Linking can be accomplished by ligation at convenient restriction sites, Gibson synthesis, or CRISPR editing. In some embodiments, a promoter is operably linked with a coding sequence when it is capable of affecting (e.g. modulating relative to the absence of the promoter) the expression of a protein from that coding sequence (i.e., the coding sequence is under the transcriptional control of the promoter). In some embodiments, operably linked nucleic acids can include chimeric nucleic acids (wherein the linked nucleic acid sequences are not naturally fused or linked together).

The term "gene leader sequence" refers to the portion of a gene that encodes for an mRNA leader sequence. The term "mRNA leader sequence" refers to the portion of an mRNA sequence that is upstream from the start of the protein coding sequence portion of the mRNA. The gene leader sequence includes, for example, the translation initiation region (TIR).

As used herein, the term "fingerloop" refers to a structure formed by an intramolecular base pairing when a nucleotide sequence and a complementary sequence thereof is present in reverse direction in the same strand and a non-complementary sequence is present there between in the same strand. The DNA fingerloop stem loop structure comprises an antisense region that binds to the target nucleic acid sequence, and the antisense region is located in the loop and in one strand of the stem loop of the DNA fingerloop stem loop structure. For example, fingerloops can refer to the stem-loop antisense motifs of DsrA that provide a modular, general purpose RNA antisense-encoding structure. For example, these fingerloops can also use DNA in place of RNA. The length of the fingerloop nucleotide sequence may be, for example, in the range from 10 nt to 150 nt, 10 nt to 100 nt, 10 nt to 75 nt, 10 nt to 50 nt, or 10 nt to 25 nt.

As used herein, the term "sRNA" or "small regulatory RNA" refers to a short-length RNA, which is usually 300 or less nucleotides in length, is not generally translated into protein, and effectively inhibits the translation and/or stability of a specific mRNA by complementary binding.

The term "mismatched" or "mismatched target sequence" refers to an off-target sequence that is not perfectly complementary to the first DNA sequence or the second DNA sequence of the chimeric deoxyribonucleic acid described herein. The dual retargeted DNA may have at least one mismatch, but can also have 2, 3, 4, 5, 6 or 7 or more mismatched nucleotides to the off-target sequence.

As used herein, the term "molecular beacon" refers a to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size. In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In die stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal.

Methods and Systems

In some aspects, disclosed herein is a method for detecting a target nucleic acid sequence, comprising the steps:
providing a nucleic acid sample from a subject;
detecting the target nucleic acid sequence using a detection probe, wherein the detection probe comprises a DNA fingerloop stem loop structure;
wherein the DNA fingerloop stem loop structure comprises an antisense region that binds to the target nucleic acid sequence;
wherein the antisense region is located in a loop and in one strand of the stem loop of the DNA fingerloop stem loop structure; and
wherein the DNA fingerloop stem loop structure diminishes base pairing to a mismatched target nucleic acid.

In some embodiments, the DNA fingerloop stem loop structure provides increased detection specificity of the target nucleic acid sequence.

In some embodiments, the detection probe is a molecular beacon. In some embodiments, the detection probe is a Northern blot probe. In some embodiments, the detection probe is a Southern blot probe.

In some embodiments, the one strand of the stem loop is the descending strand of the stem loop. In some embodiments, the one strand of the stem loop is the ascending strand of the stem loop.

In some embodiments, the antisense region that binds to the target nucleic acid sequence comprises from about 10 to about 35 nucleotides. In some embodiments, the antisense region that binds to the target nucleic acid sequence comprises from about 15 to about 25 nucleotides. In some embodiments, the antisense region that binds to the target nucleic acid sequence comprises from about 17 to about 19 nucleotides. In some embodiments, the antisense region that binds to the target nucleic acid sequence comprises from about 18 nucleotides.

In some embodiments, the length of the fingerloop nucleotide sequence may be, for example, in the range from 10 nt to 150 nt, 10 nt to 100 nt, 10 nt to 75 nt, 10 nt to 50 nt, or 10 nt to 25 nt. In some embodiments, the DNA fingerloop stem loop structure that binds to the target nucleic acid sequence comprises from about 25 to about 60 nucleotides. In some embodiments, the DNA fingerloop stem loop structure that binds to the target nucleic acid sequence comprises from about 30 to about 50 nucleotides. In some embodiments, the DNA fingerloop stem loop structure that binds to the target nucleic acid sequence comprises from about 35 to about 45 nucleotides.

In some embodiments, the number of nucleotides that base pair as part of the stem region of the stem loop of the DNA fingerloop stem loop structure comprises from about 3 to about 50 nucleotides. In some embodiments, the number of nucleotides that base pair as part of the stem region of the stem loop of the DNA fingerloop stem loop structure comprises from about 5 to about 30 nucleotides. In some embodiments, the number of nucleotides that base pair as part of the stem region of the stem loop of the DNA fingerloop stem loop structure comprises from about 7 to about 20 nucleotides. In some embodiments, the number of nucleotides that base pair as part of the stem region of the stem loop of the DNA fingerloop stem loop structure comprises from about 9 to about 15 nucleotides.

In some aspects, disclosed herein is a method for detecting a target nucleic acid sequence, comprising the steps: providing a nucleic acid sample from a subject; and detecting the target nucleic acid sequence using a detection probe, wherein the detection probe comprises a DNA fingerloop stem loop structure.

In some embodiments, the DNA fingerloop stem loop structure comprises an antisense region that binds to the target nucleic acid sequence. In some embodiments, the antisense region is located in a loop and in one strand of the stem loop of the DNA fingerloop stem loop structure. In some embodiments, the DNA fingerloop stem loop structure diminishes base pairing to a mismatched target nucleic acid.

In some aspects, disclosed herein is a method for amplifying a nucleic acid sequence, comprising the steps:
providing a nucleic acid sample from a subject;
amplifying the nucleic acid sequence using amplification primers in a polymerase chain reaction, wherein the amplification primers comprise a fingerloop stem loop structure;
wherein the DNA fingerloop stem loop structure comprises an antisense region that binds to a region flanking the nucleic acid sequence;
wherein the antisense region is located in a loop and in one strand of the stem loop of the DNA fingerloop stem loop structure; and
wherein the DNA fingerloop stem loop structure diminishes base pairing to a mismatched target nucleic acid.

In some embodiments, the amplification primers comprise from about 25 to about 100 nucleotides. In some embodiments, the amplification primers comprise from about 30 to about 80 nucleotides. In some embodiments, the amplification primers comprise from about 35 to about 60 nucleotides. In some embodiments, the amplification primers comprise from about 40 to about 50 nucleotides.

In some embodiments, the amplification is a standard polymerase chain reaction (PCR) reaction. In some embodiments, the amplification is a real-time PCR reaction. In some embodiments, the amplification is a reverse-transcription PCR reaction. In some embodiments, the amplification is a quantitative reverse-transcription PCR (qRT-PCR) reaction.

The improved nucleic acid detection methods disclosed herein can be used in a number of detection technologies. In some embodiments, the DNA fingerloops can be used to detect microorganism or pathogens in a sample. In some embodiments, the DNA fingerloops can be used to detect a DNA sequence. In some embodiments, the DNA fingerloops are used in detection probes for Southern blots. In some embodiments, the DNA fingerloops can be used to detect an RNA sequence. In some embodiments, the DNA fingerloops are used in detection probes for Northern blots. In some embodiments, the DNA fingerloops are used in detection probes for detection of mRNAs. In yet other embodiments, the DNA fingerloops are used as therapeutics, such as antivirals, for example, by binding to key sequences of an RNA virus or DNA virus to inhibit packaging or some other essential function for viral replication.

In some aspects, disclosed herein is a method for amplifying a nucleic acid sequence, comprising the steps:
providing a nucleic acid sample from a subject;
amplifying the nucleic acid sequence using amplification primers in a polymerase chain reaction, wherein the amplification primers comprise a fingerloop stem loop structure.

In some embodiments, the DNA fingerloop stem loop structure comprises an antisense region that binds to a region flanking the nucleic acid sequence. In some embodiments, the antisense region is located in a loop and in one strand of the stem loop of the DNA fingerloop stem loop structure. In some embodiments, the DNA fingerloop stem loop structure diminishes base pairing to a mismatched target nucleic acid.

In some aspects, disclosed herein is a system or a kit for measuring the activity of a chimeric deoxyribonucleic acid (DNA) in a cell, comprising:
a chimeric DNA, wherein the chimeric DNA comprises a first deoxyribonucleic acid (DNA) sequence operably linked to a second deoxyribonucleic acid (DNA) sequence;
a first plasmid comprising a first reporter gene operably linked to a first gene leader sequence; and
a second plasmid comprising a second reporter gene operably linked to a second gene leader sequence;
wherein the first DNA sequence is present in a first stem loop and the second DNA sequence is present in a second stem loop; and
wherein the first and second stem loops inhibit the binding of the first and second DNAs to mismatched target sequences.

In some aspects, disclosed herein is a method for modulating protein expression levels and/or mRNA expression levels from at least two target mRNAs in a cell simultaneously, the method comprising:
transforming the cell with a system for measuring the activity of a chimeric deoxyribonucleic acid (DNA), the system comprising:
a chimeric DNA, wherein the chimeric DNA comprises a first deoxyribonucleic acid (DNA) sequence operably linked to a second deoxyribonucleic acid (DNA) sequence;
a first plasmid comprising a first reporter gene operably linked to a first gene leader sequence; and
a second plasmid comprising a second reporter gene operably linked to a second gene leader sequence;
wherein the first DNA sequence is present in a first stem loop and the second DNA sequence is present in a second stem loop;
wherein the first and second stem loops inhibit the binding of the first and second DNAs to mismatched target sequences;
wherein the first DNA sequence binds to an mRNA of the first gene leader sequence and the second DNA sequence binds to an mRNA of the second gene leader sequence; and
measuring the protein expression levels and/or mRNA expression levels of the first reporter gene and the second reporter gene.

In some embodiments, the first DNA sequence and the second DNA sequence are comprised in at least two stem loop structures.

In some embodiments, the first DNA sequence binds to an mRNA of the first gene leader sequence. In some embodiments, the second DNA sequence binds to an mRNA of the second gene leader sequence.

In some embodiments, the first reporter gene encodes a fluorescent protein. In some embodiments, the second reporter gene encodes a fluorescent protein. In some embodiments, the chimeric DNA is from about 50 to about 300 nucleotides in length.

In some embodiments, the cell is an *Escherichia coli* (*E. coli*) cell. In some embodiments, the cell is a *Bacillus subtilis* (*B. subtilis*) cell. In some embodiments, the cell is a *Clostridium acetobutylicum* (*C. acetobutylicum*) cell. In some embodiments, the cell can be any suitable prokaryotic cell. In some embodiments, the chimeric (fingerloop) DNAs are used to test exogenous sequences in *E. coli*.

In some embodiments, the chimeric DNA binds to the at least two target mRNAs encoding at least two cell enzymes, and wherein binding results in a reduction of activity of the at least two cell enzymes.

In some embodiments, the at least two target mRNAs are in the same metabolic pathway. In some embodiments, the at least two target mRNAs are in different metabolic pathways.

In some embodiments, the chimeric DNA comprises a fingerloop (stem loop) structure. In some embodiments, the first DNA sequence and the second DNA sequence are comprised in stem-loop antisense structures. In some embodiments, the first DNA sequence and the second DNA sequence are comprised in at least two fingerloop structures.

In some embodiments, the first DNA sequence is present in a descending strand of the first fingerloop stem loop. In some embodiments, the first DNA sequence is present in an ascending strand of the first fingerloop stem loop. In some embodiments, the second DNA sequence is present in a descending strand of the second fingerloop stem loop. In some embodiments, the second DNA sequence is present in an ascending strand of the second fingerloop stem loop. In some embodiments, the first and second DNA sequences are positioned in antisense fingerloop regions.

In some embodiments, the first DNA sequence binds to an mRNA of the first gene leader sequence. In some embodiments, the second DNA sequence binds to an mRNA of the second gene leader sequence.

In some embodiments, the first reporter gene encodes a fluorescent protein. In some embodiments, the second reporter gene encodes a fluorescent protein. In some embodiments, the reporter gene is a non-fluorescent protein.

In some embodiments, the first reporter gene encodes a GFP protein. In some embodiments, the first reporter gene encodes an mCherry protein. In some embodiments, the second reporter gene encodes a GFP protein. In some embodiments, the second reporter gene encodes an mCherry protein.

In some embodiments, the chimeric DNA is from about 50 to about 300 nucleotides in length. In some embodiments, the chimeric DNA is from about 50 to about 100, from about 50 to about 150, from about 50 to about 200, from about 50 to about 250, or from about 50 to about 300, nucleotides in length.

In some embodiments, the first and second gene leader sequences target genes in the same metabolic pathway. In some embodiments, the first and second gene leader sequences target genes in different metabolic pathways. For example, the systems herein can be used to alter ATP levels while improving yield of a specific metabolite in a different pathway.

In some embodiments, the chimeric DNA binds to the at least two target mRNAs encoding at least two endogenous cell enzymes, and wherein binding results in a reduction of activity in the cell of the at least two cell enzymes. In some embodiments, the reduction in activity occurs due to the decrease in translation (and does not affect the enzyme's rate of activity directly). In some embodiments, the chimeric DNA binds to the at least two target mRNAs encoding at least two heterologous cell enzymes. In some embodiments, the chimeric DNA binds to the at least two target mRNAs encoding at least two endogenous cell enzymes.

In some embodiments, the chimeric DNA affects mRNA expression levels by modulating the stability of the target mRNA. In some embodiments, the chimeric DNA affects mRNA expression levels by blocking the access of the ribosome.

One of the important features of the DNA fingerloop is that it acts as a modular unit of antisense sequence that can be targeted to arbitrary mRNAs or to other nucleic acids (e.g., for self-assembly of RNA/DNA nanotechnological objects or devices). The fingerloop can take one of two main configurations, either with antisense sequences in the descending strand or the ascending strand of the helix as well as the loop region. These configurations can be reversed, swapped, or duplicated. For example, both stem-loops could use an ascending strand plus the loop sequence, leading to different combinations of fingerloops with varying efficacies against target mRNA gene expression, self-assembly, etc. The stem region is more tolerant to these mismatches in target sequences if the loop region is a perfect match. In addition, by increasing the intrinsic stem stability to make the stem structure longer, the off-target filtering efficiency can be improved. In other embodiments, fingerloop filtering is done in combination with toehold-sequence filtering. The toehold region is adjacent to the base of the stem.

Initial experiments used an antisense "tile" size of 18 nt. In other embodiments, 24 nt of unstructured antisense sequence can be used to increase specificity. In other embodiments, tile sizes less than 18 nt can be used to diminish the dynamic range by weakening the DNA:RNA interaction. Shorter or longer antisense "tile" sequence sizes can be used in combination with the chimeric fingerloop structure to (e.g.) repress gene expression. This antisense parameter can also be used for turning on gene expression in the context of a structured, cis-repressed mRNA translation initiation region (such as the rpoS leader; FIG. 5) that is intrinsically repressed (off-by-default) and whose expression can be activated by structural perturbation via a chimeric DNA fingerloop.

The length of the loop sequence in the fingerloop can be varied. Additional experiments can distinguish between the effects of using longer stem structures (which are more stable) and longer/shorter loop effects (which can act by varying the efficiency of helix nucleation in the target mRNA). In some embodiments, the loops are also compared so that they only partially contain antisense sequence (e.g., a loop of length 10 nt that contains 6 or 7 antisense nucleotides instead of 10 antisense nucleotides) to determine efficacy, tuning of gene expression, and to determine loop structural constraints to off-target filtering.

The chimeric DNA fingerloops are based on the structure of the native DsrA sRNA. The native DsrA sRNA contains gaps in its antisense sequence against two *E. coli* mRNA targets, rpoS and hns. The function of these gaps is not known, as engineered mismatches continue to function. The native DsrA contains both toehold-like and fingerloop-like antisense motifs which may tolerate rather than filter mismatches in loop antisense sequences. In the detection technologies described herein, in some embodiments, the gaps accelerate or modulate the kinetics of annealing.

In one aspect, it is contemplated herein that the length of the loops and stems of the fingerloop can be adjusted to optimize the scaffold. For example, the scaffold can be shortened, not adjusted, or extended at the loop by 1, 2, 3, 4, 5, 6, 7, 8, 9, 10, 11, 12, 13, 14, 15, 16, 17, 18, 19, or 20 nucleotides. Thus, in one aspect, the loop can be 5, 6, 7, 8, 9, 10, 11, 12, 13, 14, 15, 16, 17, 18, 19, 20, 21, 22, 23, 24, 25 nucleotides long. Similarly, the stem can be shortened, not adjusted, or extended by 1, 2, 3, 4, 5, 6, 7, 8, 9, 10, 11, 12, 13, 14, 15, 16, 17, 18, 19, or 20.

Additionally, the toehold can be varied by 1, 2, 3, 4, 5, 6, 7, 8, 9, 10, 11, 12, 13, 14, 15, 16, 17, 18, 19, or 20 nucleotides to increase stability. The toehold can be shortened, left unadjusted, or extended, independently of either or both the stem or loop of the fingerloop.

The use of chimeric DNAs containing two fingerloops, and the capacity to target more than two mRNAs, shows that synthetic multi-fingerloop chimeric DNAs can be built for targeting and coordinating expression from larger numbers of genes. In some embodiments, 4-fingerloop chimeric DNAs using the genetic system disclosed herein with fluorescent reporters are used. In some embodiments, the buk' and hydA' fingerloops are built onto the 5'-end of native DsrA structure to create a chimeric DsrA-like DNA with 4-mRNA targeting (for example, rpoS, hns, buk, hydA).

Applications of these multi-acting chimeric DNAs include tuning pathway gene expression for metabolic engineering of strains, for example coordinating multiple mRNAs in single or multiple/different pathways, for increasing fermentation product yields, fermentation selectivity, minimizing toxicity, and/or balancing cellular health and growth rates. Further, combinatorial knocking-down of multiple mRNAs (including essential genes that cannot be conventionally knocked out) can be used, for example, in screening drug targets in pathogens, for determining metabolic flux parameters in bacterial strains for metabolic engineering, and for producing probiotic or commensal bacterial strains.

The region of the chimeric DNAs between stem-loops 1 and 2 can form base pairs with several native mRNA targets of DsrA. Thus, like the loop portion of the fingerloop, these single-stranded "toehold" regions could act as a filter of off-target DNA:mRNA interactions in the event of a target mismatch.

This concept of a "toehold" dates from earlier work with nanoscale DNA "devices" that use DNA:DNA hybridization. Here the "toehold" region is a single-stranded region of nucleic acid that constitutes part of an antisense sequence that is complementary to a target DNA (or RNA). The other part of this antisense sequence is capable of base pairing to a target but is involved in pairing to a competitor "sink" nucleic acid strand sequence that is to be displaced. The scheme is such that "toehold" pairing to a target initiates a strand displacement reaction of the competitor in a way that would otherwise be kinetically unfavorable without the toehold. This scheme works because the nucleation of nucleic acid base pairing interactions is kinetically limiting, but the subsequent strand displacement or "branch migration reaction" is very fast. This "strand displacement reaction" then frees the full antisense sequence to pair with the target sequence at a higher final stability (lower free energy), thus the full pairing reaction is thermodynamically favorable.

In some embodiments, "toehold switches" have been used in mRNAs genetically in cis, to sense trans-acting antisense RNA signals and activate translation of target genes fused to the toehold switch, or to permit the expression of miRNA regulators. The context of toehold-mediated strand displacement can be calibrated by introducing gaps in the sequence complementarity and by adjusting other parameters. The "toehold switch" cannot act in trans, and is distinct from the idea of a toehold sequence that is complementary and thus it is distinct from trans-acting DNAs or sRNAs.

There is a relationship between the efficacy of DNA fingerloop gene-repression activity in vivo and the free energy parameters of both the fingerloop (self-pairing) and the fingerloop-target interactions. The thermodynamic driving force for pairing of fingerloop and target is related (or proportional) to the differences in stability of the self-paired structure of the fingerloop, the self-paired structure of the target mRNA, and the final stability of the paired complex. Factors that can contribute to stability of various forms are: (a) The length and strength of the fingerloop stem sequence, including its base pair composition; (b) the existence, if any, of mismatches, bulges, and other non-canonical base pairs in the stem; (c) the length, sequence composition and structure, if any, of both the antisense and target regions; (d) the length and strength of the duplex formed between the fingerloop and its target; (e) the length, strength and composition of the loop region of the fingerloop; (f) the fraction of the loop sequence that contains antisense sequences, since extra sequence could be included in this loop outside the antisense sequence; (g) the length, strength and sequence composition of a toehold sequence adjacent to the stem, and the complex formed between the toehold and the target; (h) the type, location and number of mismatches or bulged nucleotides formed between the chimeric DNA and its target; (i) the cooperativity, if any, between the toehold:target and fingerloop:target interactions.

In some embodiments, DNA fingerloops can be delivered to a cell by leveraging existing cellular uptake means such as endocytosis, and can be carried on a nanoparticle made of RNA, DNA or other material.

In other embodiments, DNA fingerloops can be packaged in a phage or viral capsid, envelope, liposome, or other delivery matrix, and can thereby be taken up into a cell.

In some embodiments, the chimeric DNA can comprise at least one chemically modified nucleotide. Various chemically modified nucleotides are known in the art, for example, see WO/2018/009822.

In one embodiment, the at least one chemically modified nucleotide is a chemically modified ribose. In one embodiment, the chemically modified ribose is selected from 2'-O-methyl (2'-O-Me), 2'-Fluoro (2'-F), 2'-deoxy-2'-fluoro-beta-D-arabino-nucleic acid (2'F-ANA), 4'-S, 4'-SFANA, 2'-azido, UNA, 2'-O-methoxy-ethyl (2'-O-ME), 2'-O-Allyl, 2'-O-Ethylamine, 2'-O-Cyanoethyl, Locked nucleic acid (LAN), Methylene-cLAN, N-MeO-amino BNA, or N-MeO-aminooxy BNA. In one embodiment, the chemically modified ribose is selected from 2'-O-methyl (2'-O-Me) or 2'-Fluoro (2'-F). In one embodiment, the chemically modified ribose is 2'-O-methyl (2'-O-Me). In one embodiment, the chemically modified ribose is 2'-Fluoro (2'-F).

In one embodiment, the at least one chemically modified nucleotide is a chemically modified nucleobase. In one embodiment, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine ($\Psi$), $N^1$-methylpseudouridine (me$^1\Psi$), $N^6$-methyladenosine (me$^6$A), or thienoguanosine ($^{th}$G).

In one embodiment, the at least one chemically modified nucleotide is a chemically modified phosphodiester linkage. In one embodiment, the chemically modified phosphodiester linkage is selected from phosphorothioate (PS), boranophosphate, phosphodithioate (PS2), 3',5'-amide, N3'-phosphoramidate (NP), Phosphodiester (PO), 2',5'-phosphodiester (2',5'-PO) or morpholino (phosphorodiamidate morpholino oligomer). In one embodiment, the chemically modified phosphodiester linkage is phosphorothioate.

Other modified nucleoside analogues can be found in US20080261823 titled "Fluorescent Nucleoside Analogs That Mimic Naturally Occurring Nucleosides" by inventor Yitzhak Tor.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. DNA Fingerloops

DNA fingerloops can contain the novel structural sequence-discrimination function that are found in RNA fingerloops. DNA:DNA interactions are tested with a target oligodeoxynucleotide (ODN) molecule containing (e.g.) the hydA leader sequence equivalent to that used in sRNA experiments (See FIG. 1 and FIG. 2). DNA sequences equivalent/analogous to sRNA fingerloop sequences are used to determine the base pairing and off-target discrimination functions of DNA fingerloops. One assay compares the DsrA-hydA'2.4.1 fingerloop antisense sequence to an unstructured antisense sequence alone in their abilities to bind the target ODN or point mutant derivatives of the target ODN. The binding assay is initially a native gel mobility-shift assay, as bound complexes migrate slower than unbound ODNs on a non-denaturing acrylamide gel held at low temperature (~8° C. to ~6° C.). Additional experiments use "molecular beacon"-type fingerloops to measure the kinetics and equilibrium of DNA:DNA (or DNA:RNA) association. Here, the fingerloop DNA stem structure can open as the antisense sequence pairs with its target partner, separating the stem strands. Molecular beacons are sensitive indicators of these kinds of structural transitions and are monitored with stop-flow fluorimetry and other tools for fast, precise measurement of association kinetics. Experiments can also be monitored in 96-well or 384-well plate reader formats for higher throughput screening.

DNA fingerloops can be used as PCR primers. Here the loop and descending strand of the stem-loop are complementary/anti-sense to a desired target DNA sequence (or RNA sequence, for RT-PCR). The loop region acts via a mismatch filtering mechanism to increase the specificity of PCR amplification. The remainder of the antisense region is at the 3'-end of the fingerloop primer, and mismatches here are further filtered by the inability of the polymerase to recognize and form a priming complex with a template that is mismatched near the 3'-end. Thus, the fingerloop extends the length of the mismatch-excluding sequence and thereby increases the specificity of PCR. The stability of the DNA stem can be increased or decreased by varying the stem-loop length, by varying the antisense sequence length, and/or by varying the loop size and the fraction of the loop that contains antisense sequences. An optimal melting temperature for the PCR reaction is determined to achieve filtering via fingerloop PCR primers. A pair of DNA-fingerloop based PCR primers can be used to filter out off-target interactions and discriminate between multiple target amplicons in a mixture of templates. Further, the filtering ability can be used to multiplex the PCR reaction, using multiple primer pairs simultaneously in one reaction, enabling subsequent detection by various means (gels, fluorescent readout, etc.) of a mixed population of different cells. This application is tremendously powerful in PCR-based diagnostics to indicate the type and number of different species in a sample of cells, for example to determine etiology of illness or to identify and enumerate a population of gut bacteria in a patient. Another powerful application of this technology is for DNA fingerprinting for forensics and paternity testing. As the DNA fingerloop stem loop structures can decrease mismatches, this technology is important where inappropriate detection of mismatches has life-altering consequences.

Example 2. DNA Fingerloop Structures Diminish Base Pairing to Mismatched Target

In order to determine if chimeric DNA sequences contained in stem loop structures could diminish base paring to mismatched targets, gel shift experiments were conducted to compare fingerloop stem loops to linear antisense probes. In addition, wild type and mutant (single mismatch) DNA sequences were analyzed as well.

As shown in FIG. 1, antisense RNAs were designed to analyze whether fingerloop stem loop structures can be used to diminish base pairing to mismatched targets.

Figure 2:
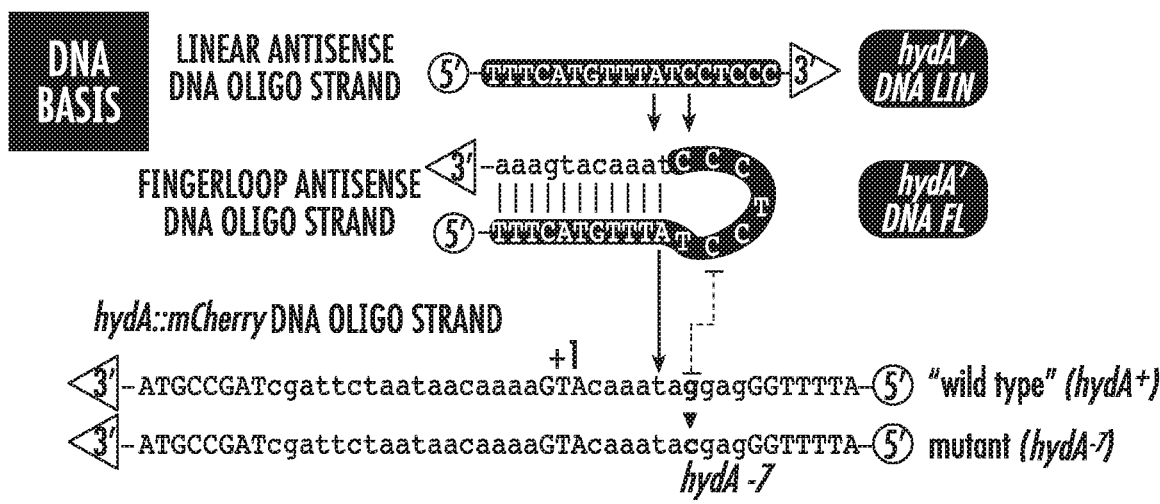
FIG. 2. Overview of the fingerloop DNA structure and mismatch exclusion activity, analogous to the RNA phenomenon. A linearized antisense sequence (DNA LIN, above) is compared to the fingerloop DNA stem-loop (DNA FL) for annealing to two single-stranded DNA target analogs of hydA, namely the wild type (hydA+) and a mismatch mutant (hydA-7). This hydA-7 mismatch coincides with the antisense position in the fingerloop loop. This mismatch blocks formation of a fingerloop DNA/hydA target complex, whereas the linearized antisense (LIN) probe is capable of tolerating the mismatch. Thus, the fingerloop excludes complex formation with mismatched target DNAs, demonstrating fingerloop mismatch exclusion is a phenomenon of both RNA and DNA. The sequences found in FIG. 2 are TTTCATGTTTATCCTCCC (SEQ ID NO: 3), TTTCATGTTTATCCTCCCtaaacatgaaa (SEQ ID NO: 4), ATTTTGGgaggataaacATGaaaacaataatcttagcTAGCCGTA (SEQ ID NO: 5), and ATTTTGGgagcataaacATGaaaacaataatcttagcTAGCCGTA (SEQ ID NO: 6).

As shown in FIG. 2, antisense DNAs were also tested whether they can be used to show that the fingerloop stem loop structures can be used to diminish base pairing to mismatched targets.

Figure 9:
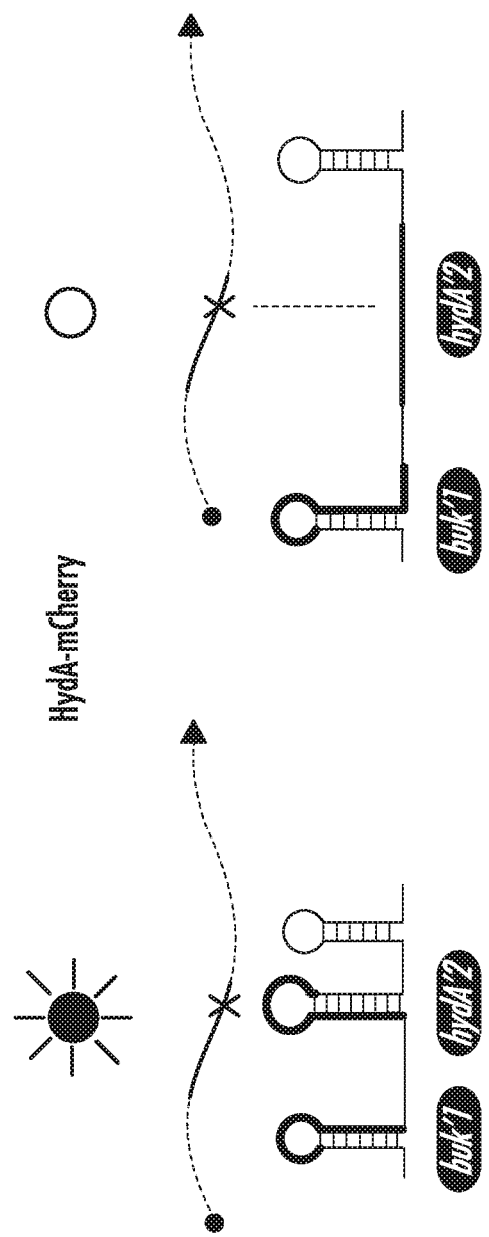
FIG. 9. General scheme to test hybridization filtering using reporter genes in vivo. On the left, a structured probe (hydA'2) cannot interact with a reporter gene that mismatches in such a way that the mismatch occurs in the loop region of a hairpin stem-loop structure. In contrast, a linearized hydA'2 probe (right) will tolerate the mismatch and will deactivate the reporter gene, decreasing the level of red fluorescent protein produced. Comparison of the two types of probes (fingerloop stem-loop versus linear antisense probe) reveals the mismatch exclusion or hybridization filtering function of the fingerloop.
Figure 11A:
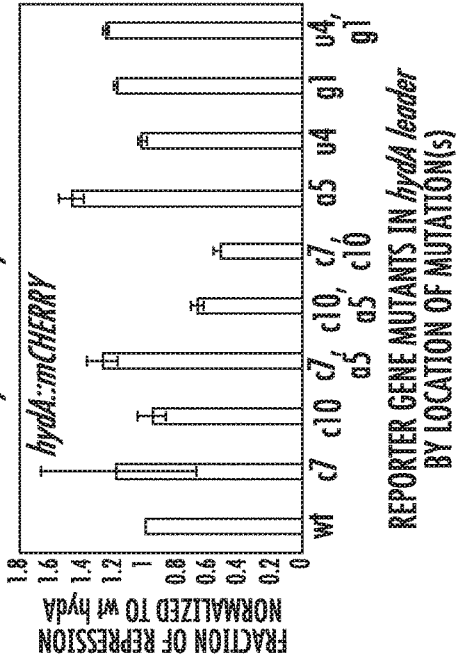
FIGS. 11A-11D. Fingerloop filters off target mRNA hybridization.
Figure 11B:
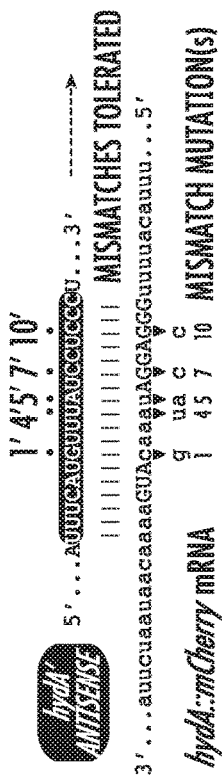
Figure 11C:
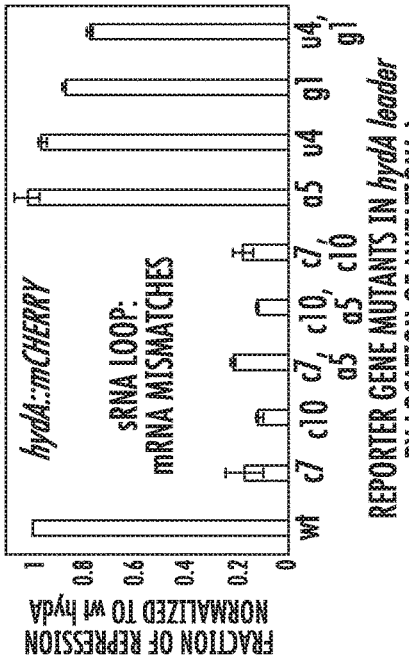
Figure 11D:
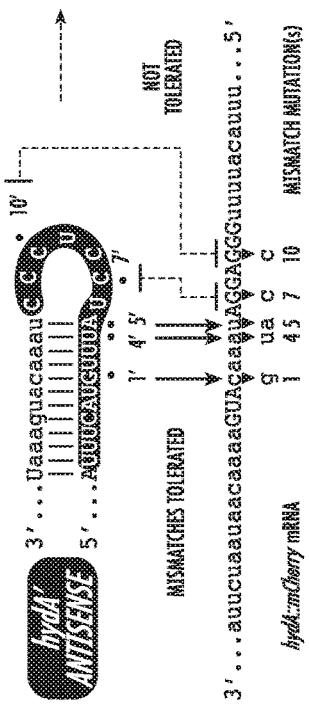

As shown in FIG. 9, hybridization filtering experiments are used to compare fingerloop stem loop structures compared to unstructured equivalent DNAs. The fluorescent reporter hydA-mCherry is used in the example here. The stem strand acts as a sink competitor for the mRNA target and filters out mismatches.

Figure 12:
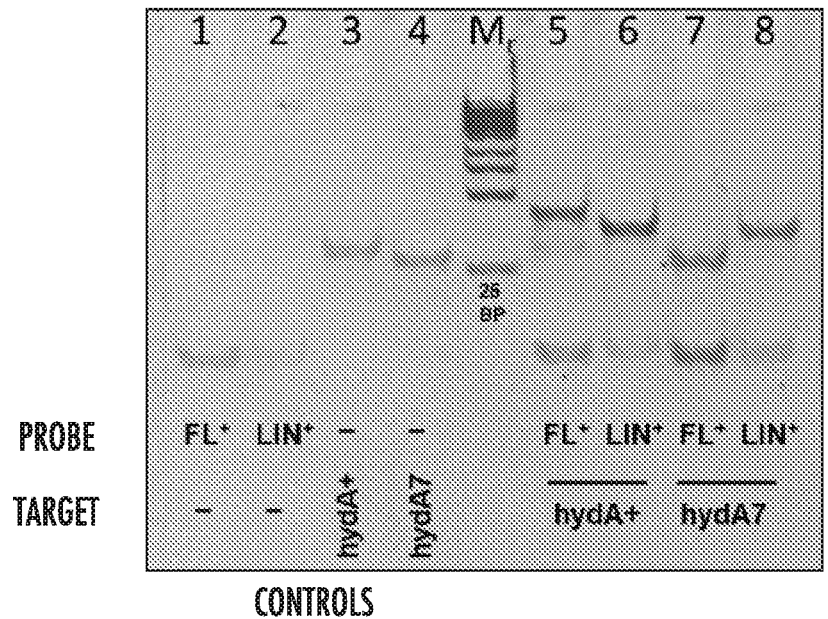
FIG. 12. DNA mobility shift experiment demonstrates DNA fingerloop mismatch-exclusion activity. Gel: Lanes 1-4: Controls (not annealed). DNA oligos of (lane 1) fingerloop antisense, (lane 2) linearized antisense, and hydA target variants (lane 3, +=wild type; lane 4, −7=mismatch mutant). The mismatch mutant is in a location corresponding to stem position in fingerloop (see FIG. 2 for structural representations of these oligos and their sequences). Lane 4: molecular mass marker, 25 base pairs for lowest band. Lanes 5-6 show the effect of mixing the hydA+ target with either fingerloop (lane 5) or linear (lane 6) antisense probes. Lane 7: Fingerloop does not form a complex with the hydA7 mutant, whereas the linearized antisense oligo tolerates the mismatch and forms a complex (lane 8). Contents of each lane and the presence/absence of a gel-shifted complex are summarized below in a table.
Figure 13:
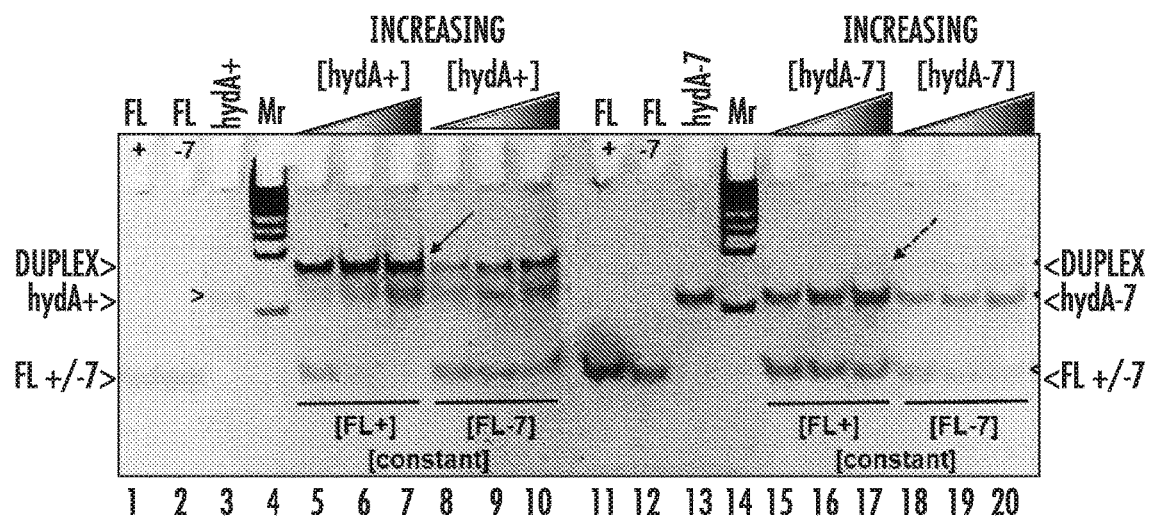
FIG. 13. Titration of increasing concentrations of target (hydA) DNA establish different thresholds for fingerloop/target binding and gel-shifted complex formation. Fingerloop DNAs ("wild type" FL+ or mutant FL-7) were annealed with an increasing concentration of either hydA+ target or the mutant derivative hydA-7, and DNAs were analyzed on a gel. The target hydA+ or hydA-7 were increased in concentration (1, 2, 4×) over each series. The variant FL-7 probe has a mutation in the loop that is an exact antisense match for the hydA-7 mutant target. Controls: lanes 1-3 and 11-13 are single species without annealing. Lanes 4 and 14 are molecular weight markers (25 bp lowest band). Carets (>) indicate individual species. DUPLEX indicates a gel-shifted DNA complex of a FL DNA and a hydA target. Horizontal solid arrow indicates a gel-shifted complex; dotted horizontal arrow indicates the expected migration position of such complexes not strongly seen in lanes 15-17 due to filtering of mismatches. The FL+ species is able to form complexes with the hydA+ species (lanes 5-7) but not with the hydA-7 species (lanes 15-17) even at highest concentrations, presumably due to mismatch exclusion. The FL-7 species is partially able to form complexes with the hydA+ target (lanes 8-10), but only poorly and at high concentrations when compared to the FL+/hydA+ target (lanes 5-7). The FL-7/hydA-7 complex forms only poorly (lanes 18-20).
Figure 14A:
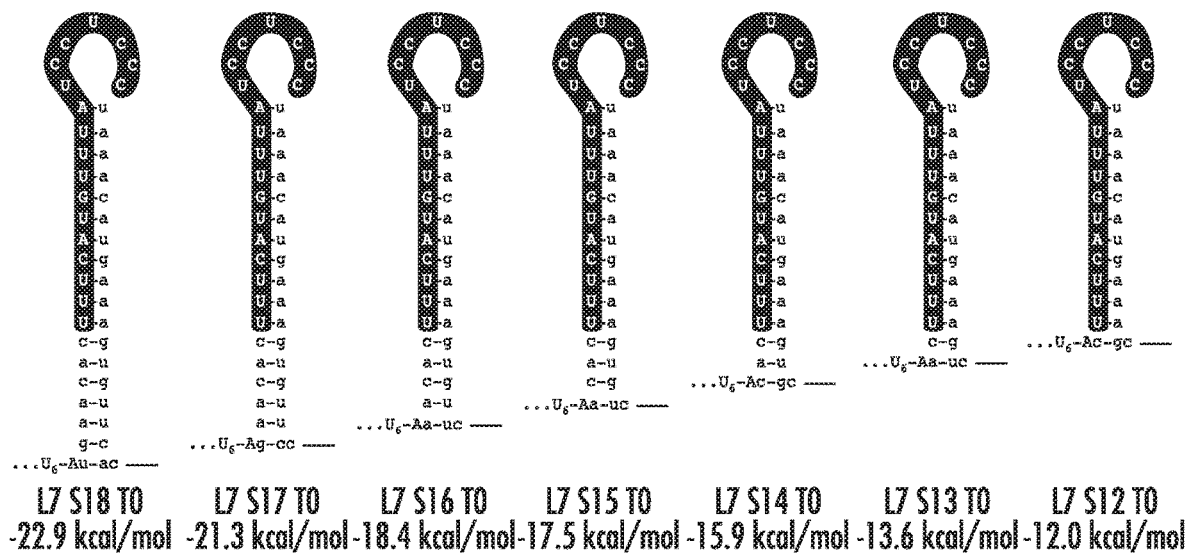
FIGS. 14A-14D. Fingerloop RNA stem vs. loop parameters have different contributions to function. The in vivo genetic system was used to evaluate RNA fingerloops in DsrA sRNA by their activity at the hydA-mCherry (wt) reporter gene. For experiments with DNA fingerloops the L7 S16 fingerloop (panel A, third from left) served as the basis for further experiments in vitro.
Figure 14B:
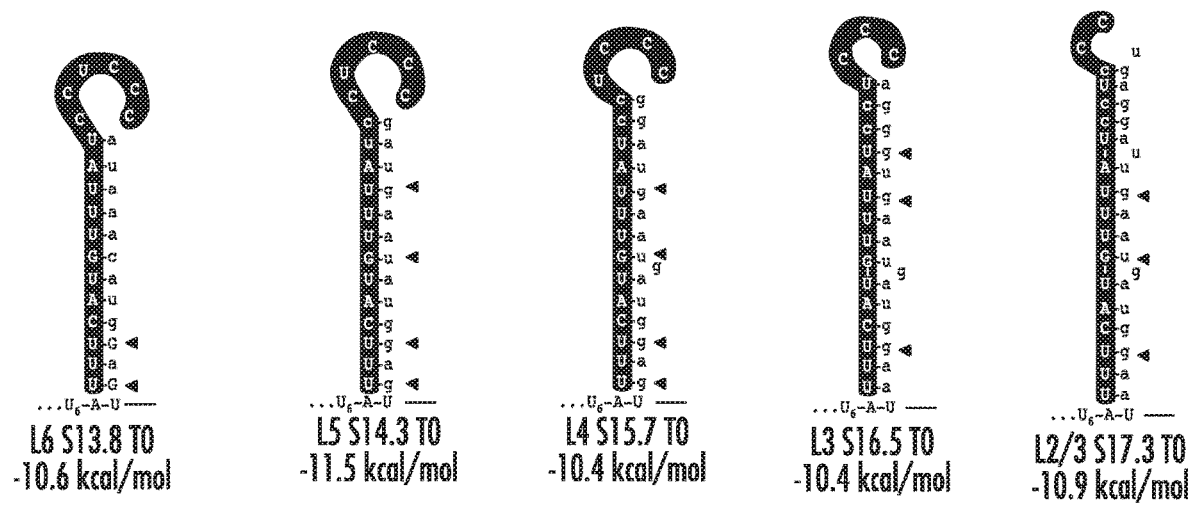
Figure 14C:
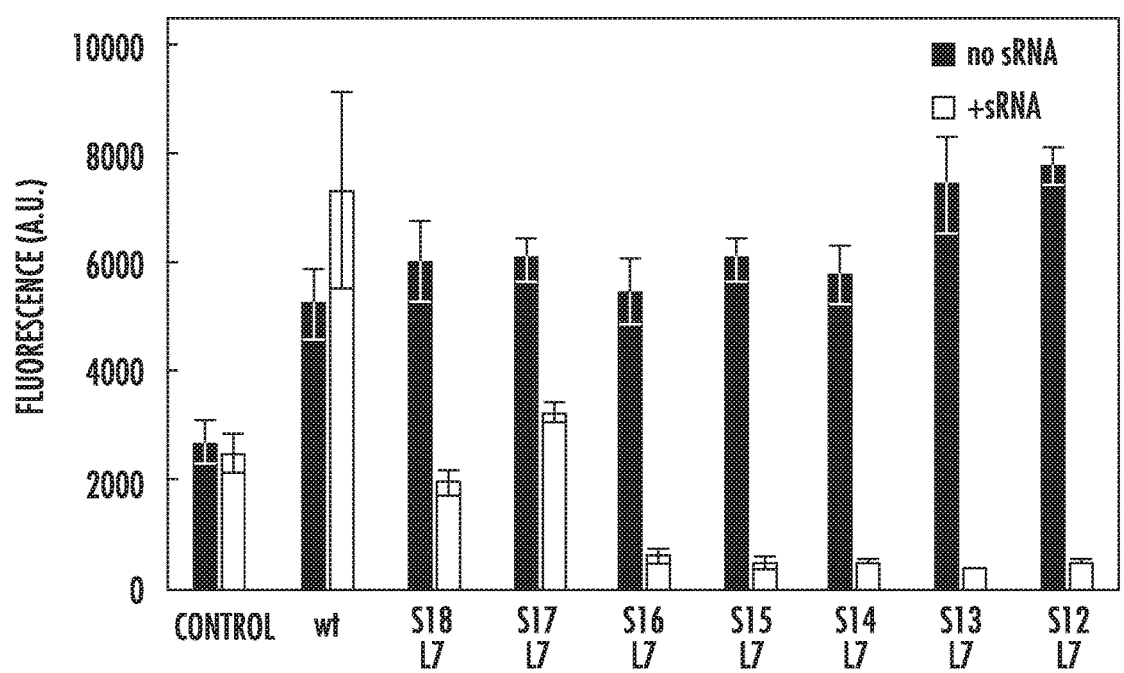
Figure 14D:
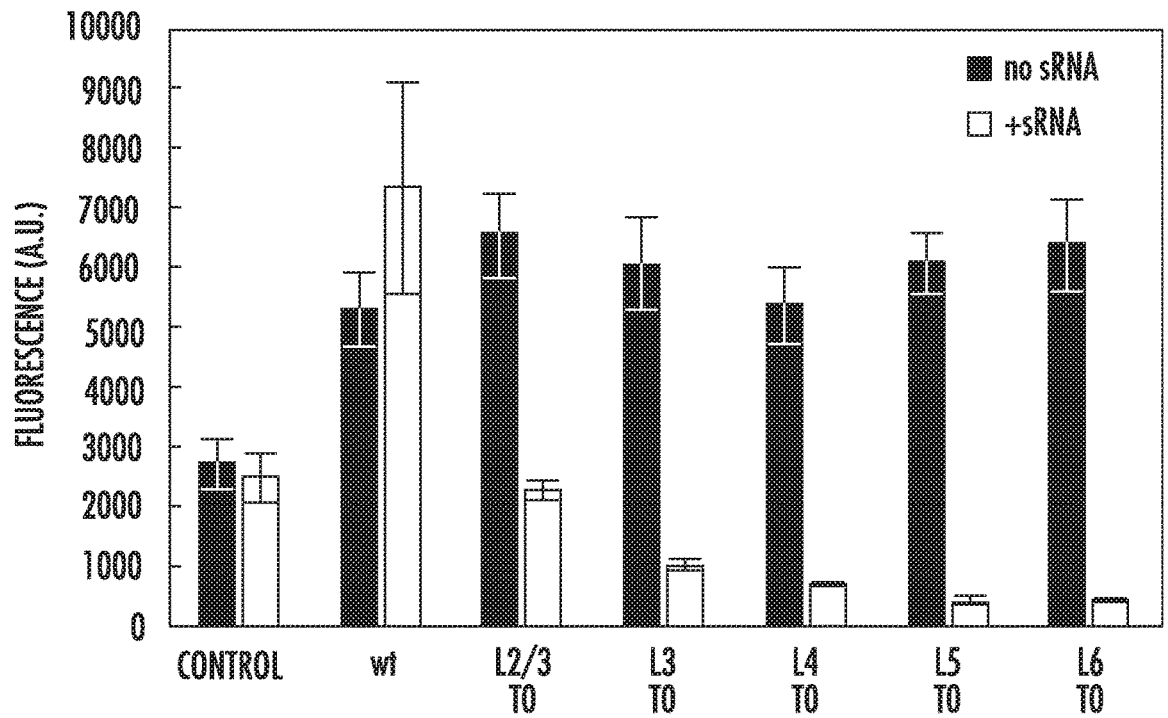
Figure 15A:
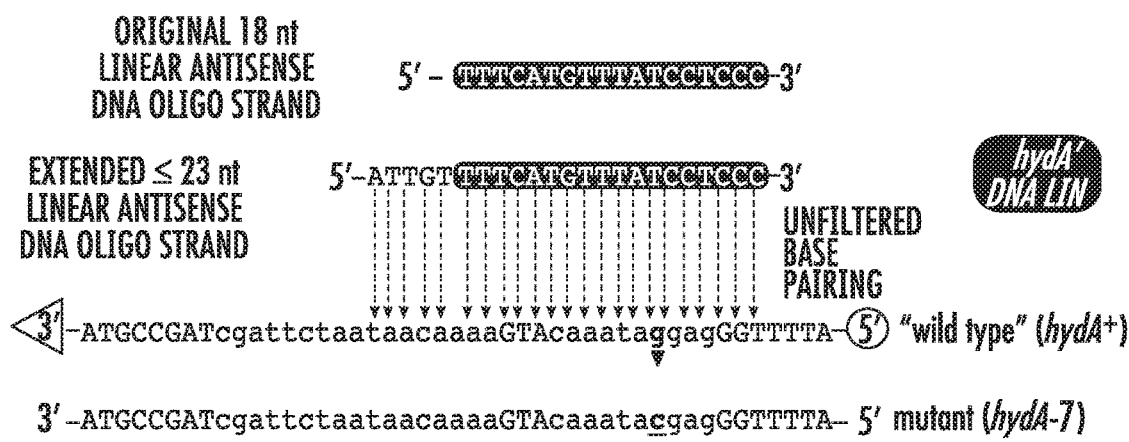
FIGS. 15A-15C. Probe design for optimization of mismatch exclusion and antisense sequence length in DNA fingerloops.
Figure 15B:
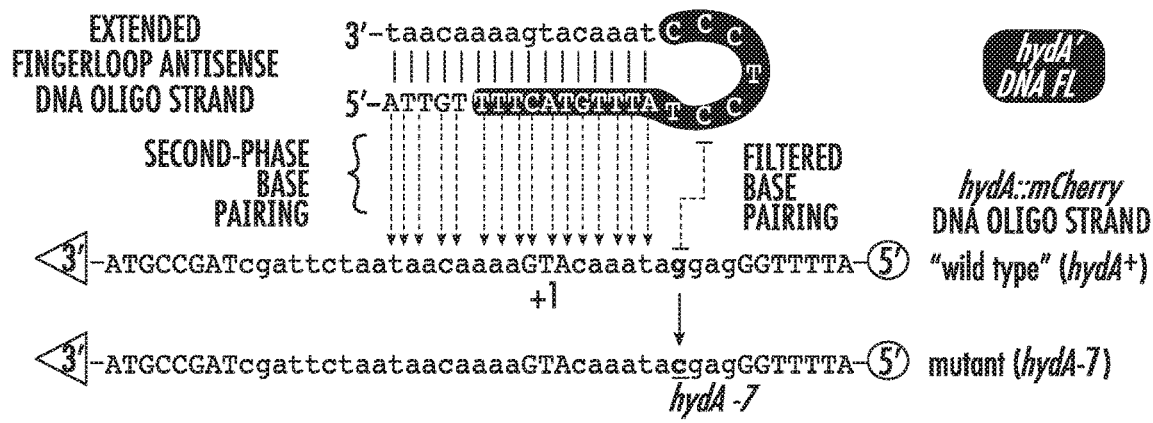
Figure 15C:
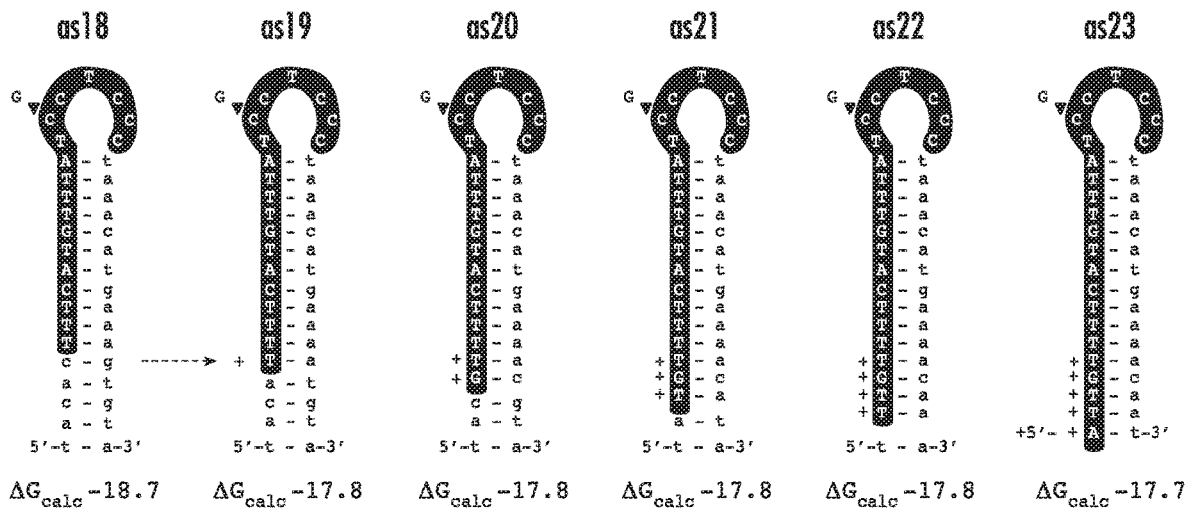
Figures 16A, 16B, 16C:
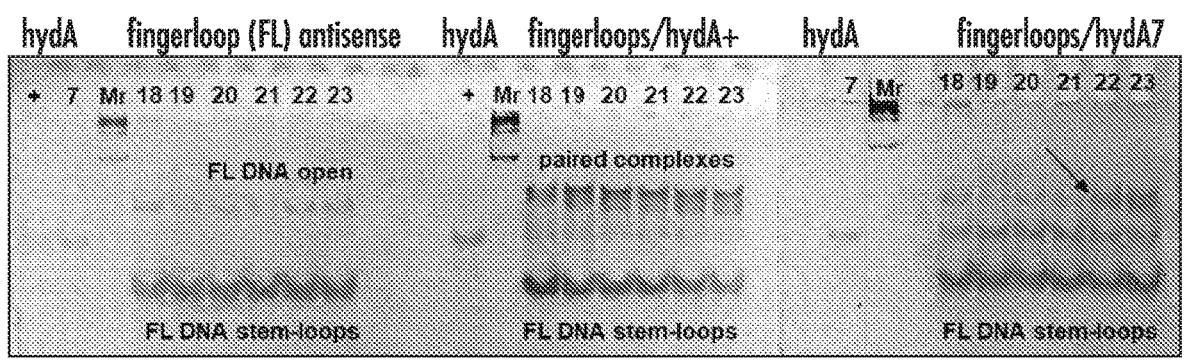
FIGS. 16A-F. Analysis of probe length effects on mismatch exclusion activity of antisense fingerloop vs. antisense linear probes. Reactions were carried out at room temperature. Above (A-C): fingerloops; below (D-F): linear antisense probes. Left gel panels (A,D) for each set are individual DNA oligos as controls for migration in a gel. Central panel for both sets (B,E) are gel-shift experiments with the hydA+ probe. Right gel panels (C, F) are gel-shift experiments with the hydA-7 mismatched probe. Diagonal arrows show the position of gel-shifted complexes for the fingerloop and linearized probes with hydA-7 mismatch. Notably, fingerloop probes only poorly form gel-shifted complexes (beyond a small percentage of the population), and only at antisense length above 22 nucleotides. The linear probes are less discriminating and readily form gel-shifted complexes at antisense lengths of 20 nucleotides and above. Acrylamide gels (15%, 19:1 acrylamide: bis in 0.5× TBE buffer) were run at room temperature and stained with GelRed.
Figures 16D, 16E, 16F:
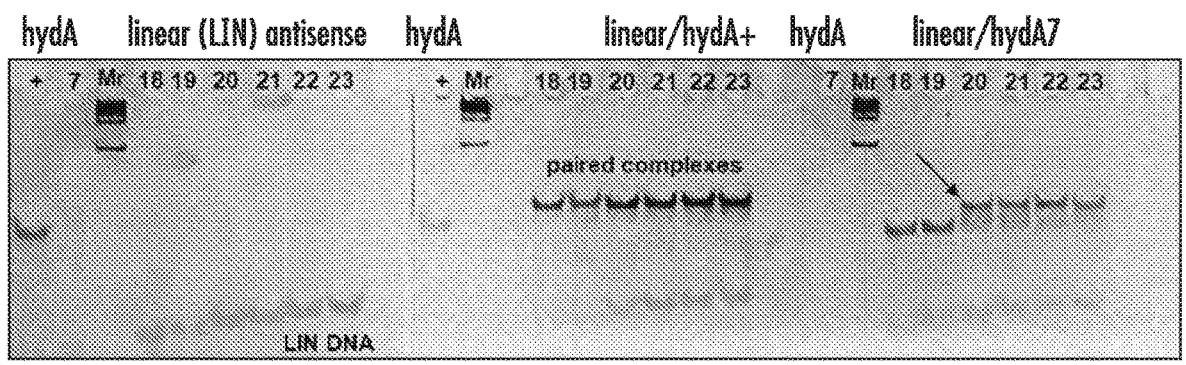

As shown in FIG. 12, gel-shift experiments found that DNA fingerloop stem loop structures can be used to diminish base pairing to mismatched targets. In particular, lane 7 shows that the fingerloop DNA does not hybridize with the mismatched (hydA-7) target and does not produce a gel-shifted complex. Nucleic acids were run on a 15% polyacrylamide (19:1 bis), 0.5× TBE gel, and stained with GelRed stain. The photograph of the gel was taken with a red filter, and inverted to a black and white image as shown using Adobe PS. Contents of the gel lanes in the gel shift experiment are described at the bottom of FIG. 12.

Example 3. Chimeric DNAs

FIG. 3 shows a dual-acting retargeted chimeric DNAs. To coordinate two simultaneous interventions in a metabolic pathway, a retargeting system was developed for assaying dual-acting chimeric DNAs. A particular metabolic engineering intervention can inform the choice of two target mRNAs to be tuned by coordinate regulation (e.g., improved n-butanol fermentation selectivity and yield; buk and hydA mRNAs of *Clostridium acetobutylicum*) using a retargeted chimeric DNA (right). Retargeted antisense "fingerloop" library variants based on the DsrA scaffold are designed to pair with these mRNA targets. The mRNAs to be tested are prepared as fusions with two fluorescent reporter genes, and effects of chimeric DNA variants are quantified during expression in *E. coli*.

FIG. 5 shows a schematic for the system using the chimeric DNAs to affect gene expression. The chimeric DNA activates an intrinsically repressed rpoS transcript reporter fusion and enhances the turnover of hns transcript fusions. Gray paired circles represent ribosomes. Circled numbers indicate DNA:RNA interactions via individual stem-loop structures 1 and 2.

Figure 6:
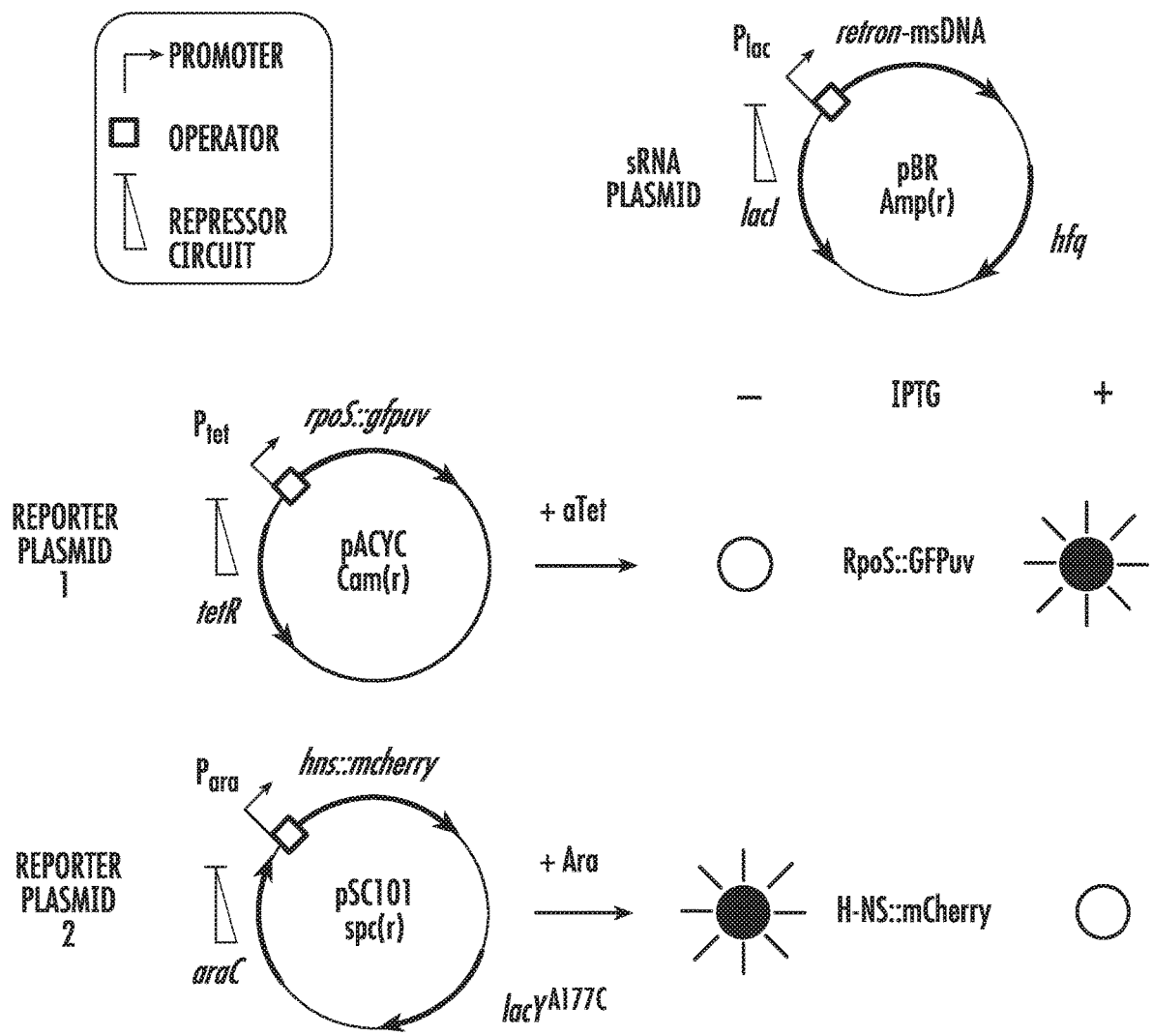
FIG. 6. Genetic system for characterization of chimeric DNA activity at multiple targets. All three transcripts originate from separate, compatible plasmids, and these transcripts are controlled with orthogonal repressor protein/inducer pairs. Blue arrows represent repressor proteins; blue lines represent inducible repressor circuits. Orange arrows represent additional protein factors in the system (hfq, lacY$^{A177c}$). (Plasmid 1) Transcription of translationally cis-repressed rpoS::gfp$_{uv}$ (green) is induced with anhydrotetracycline (aTet), giving low/no green fluorescence signal. (Plasmid 2) Transcription of hns::mCherry (red) is induced with arabinose (Ara) and gives a strong red fluorescence signal. (Plasmid 3) Chimeric DNA antisense molecules (above) are induced with IPTG (+) and increases translation of GFP to produce a strong green signal, whereas DsrA antagonizes the translation of mCherry (open and "flashing" filled circles). This system is based on an analogous system (Lahiry et al. 2017) that uses small regulatory RNAs (sRNAs) in E. coli to achieve similar screening of antisense sRNA function.
Figure 7A:
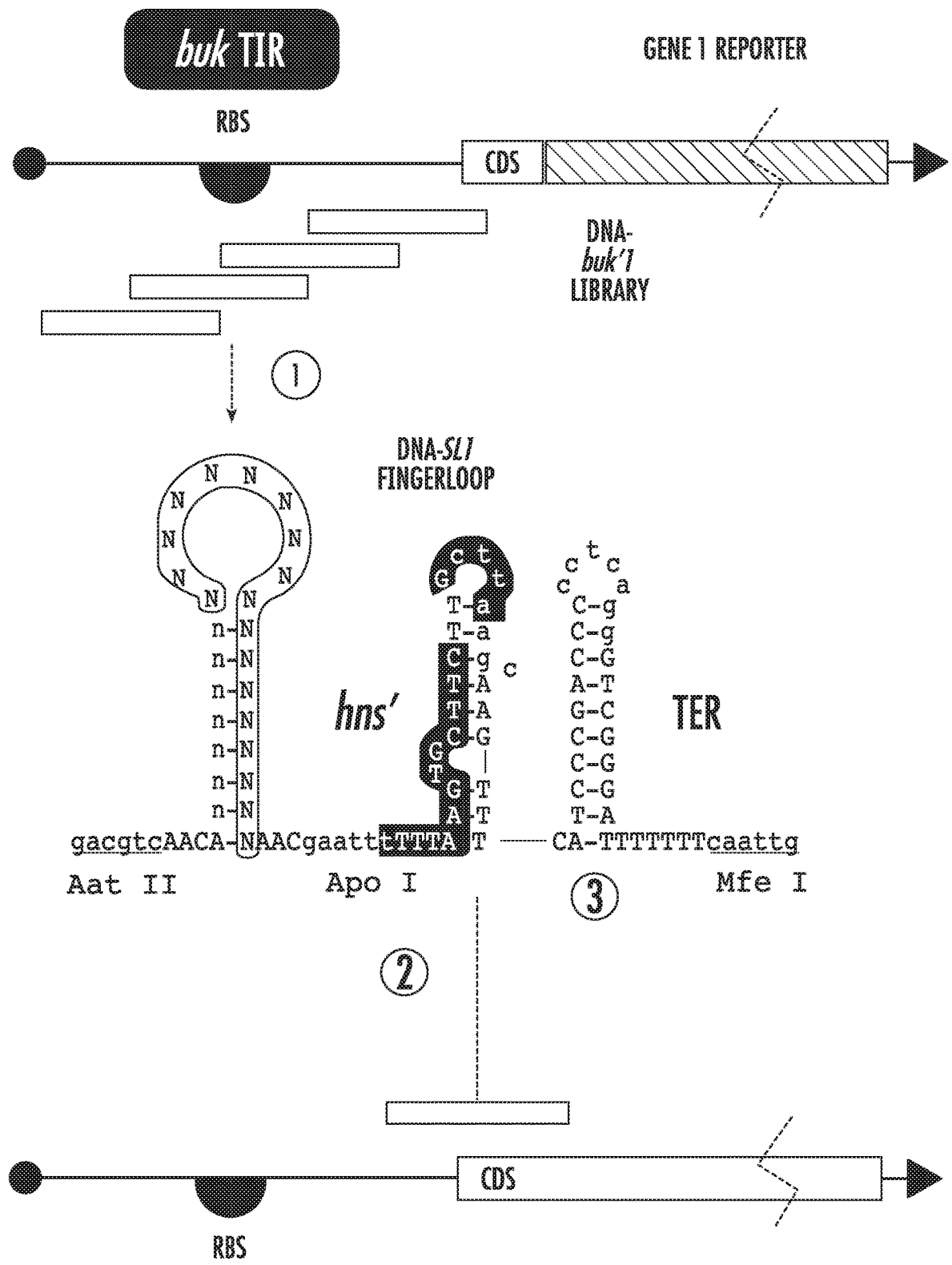
FIGS. 7A-7B. Scheme for retargeting DsrA via fingerloop antisense-motif libraries. The location of the antisense sequences of the DsrA antisense RNA scaffold structure are highlighted on a cartoon structure diagram (cf.
Figure 7B:
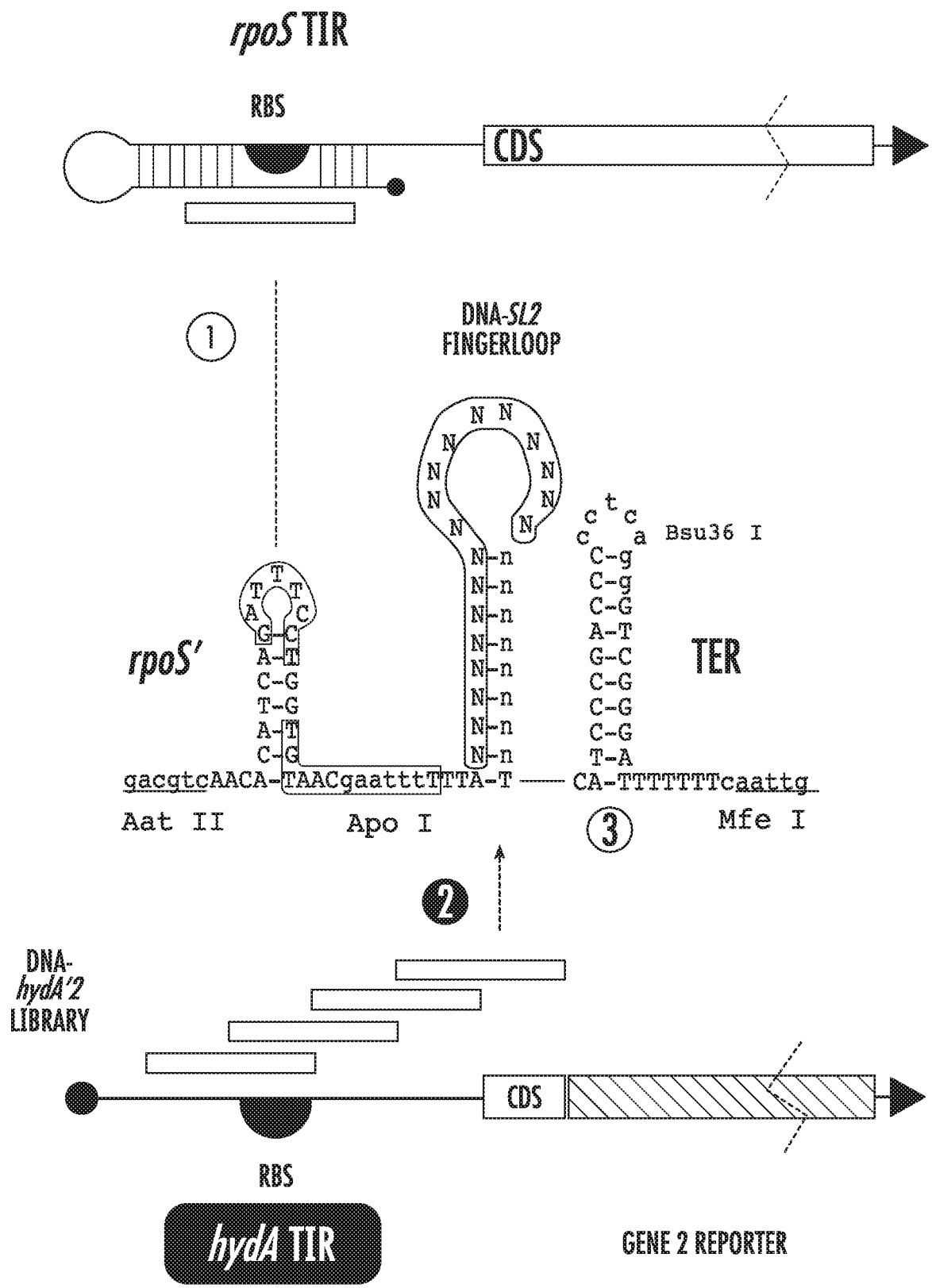
Figures 8A, 8B:
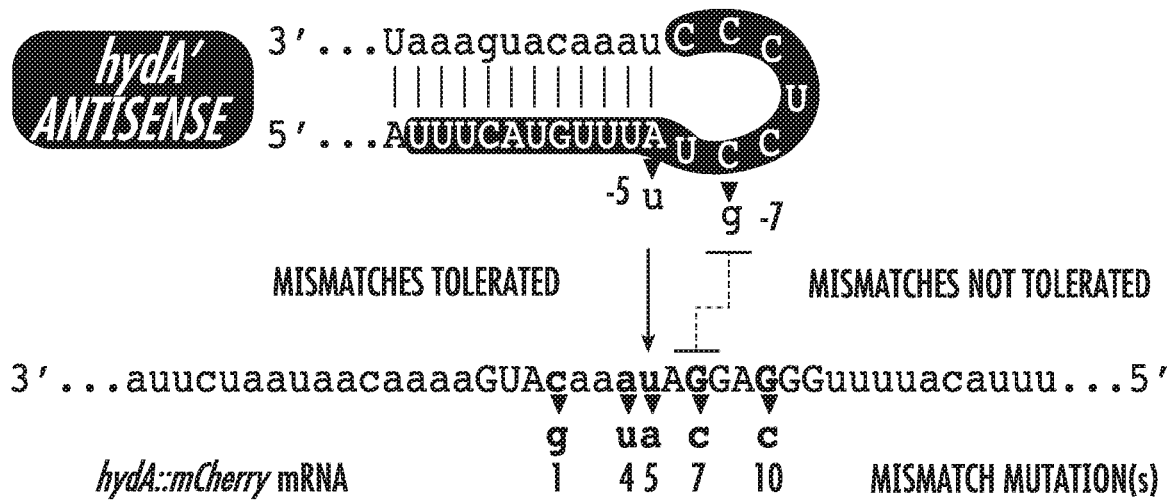
FIGS. 8A-8B. RNA Fingerloop activity by sRNA:mRNA interaction is confirmed; suggests special role for loop interactions.

FIG. 6 shows a genetic system for characterization of chimeric DNA activity at multiple targets. The target mRNA transcripts originate from separate, compatible plasmids, and these transcripts are controlled with orthogonal repressor protein/inducer pairs. Transcription of translationally cis-repressed rpoS::gfp$_{uv}$ is induced with anhydrotetracycline (aTet), giving low/no green fluorescence signal. Transcription of hns::mCherry is induced with arabinose (Ara) and gives a strong red fluorescence signal. The chimeric DNA increases translation of GFP to produce a strong green signal, whereas the chimeric DNA antagonizes the translation of mCherry (open and "flashing" filled circles).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

I claim:

1. A method for modulating protein expression levels and/or mRNA expression levels from at least two target mRNAs in a cell simultaneously, the method comprising:
    transforming the cell with a system for measuring the activity of a chimeric deoxyribonucleic acid (DNA), the system comprising:
        a chimeric DNA, wherein the chimeric DNA comprises a first deoxyribonucleic acid (DNA) sequence operably linked to a second deoxyribonucleic acid (DNA) sequence;
        a first plasmid comprising a first reporter gene operably linked to a first gene leader sequence; and
        a second plasmid comprising a second reporter gene operably linked to a second gene leader sequence;
    wherein the first DNA sequence is present in a first stem loop and the second DNA sequence is present in a second stem loop;
    wherein the first and second stem loops inhibit the binding of the first and second DNAs to mismatched target sequences;
    wherein the first DNA sequence binds to an mRNA of the first gene leader sequence and the second DNA sequence binds to an mRNA of the second gene leader sequence; and
    measuring the protein expression levels and/or mRNA expression levels of the first reporter gene and the second reporter gene.

2. The method of claim 1, wherein the first DNA sequence and the second DNA sequence are comprised in at least two stem loop structures.

3. The method of claim 1, wherein the first DNA sequence binds to an mRNA of the first gene leader sequence.

4. The method of claim 1, wherein the second DNA sequence binds to an mRNA of the second gene leader sequence.

5. The method of claim 1, wherein the first reporter gene encodes a fluorescent protein.

6. The method of claim 1, wherein the second reporter gene encodes a fluorescent protein.

7. The method of claim 1, wherein the chimeric DNA is from about 50 to about 300 nucleotides in length.

8. The method of claim 1, wherein the cell is an *Escherichia coli* cell.

9. The method of claim 1, wherein the cell is a *Clostridium acetobutylicum* cell.

10. The method of claim 1, wherein the at least two target mRNAs are in different metabolic pathways.

* * * * *

SEQUENCE LISTING

```
<160> NUMBER OF SEQ ID NOS: 49

<210> SEQ ID NO 1
<211> LENGTH: 31
<212> TYPE: RNA
<213> ORGANISM: Artificial Sequence
<220> FEATURE:
<223> OTHER INFORMATION: Synthetic construct

<400> SEQUENCE: 1
auuucauguu uauccuccccu aaacaugaaa u                          31

<210> SEQ ID NO 2
<211> LENGTH: 45
<212> TYPE: RNA
<213> ORGANISM: Artificial Sequence
<220> FEATURE:
<223> OTHER INFORMATION: Synthetic construct

<400> SEQUENCE: 2
uuuacauuuu gggcaggcau aauaacgaug aaaacaauaa ucuua            45

<210> SEQ ID NO 3
<211> LENGTH: 18
<212> TYPE: DNA
<213> ORGANISM: Artificial Sequence
<220> FEATURE:
<223> OTHER INFORMATION: Synthetic construct

<400> SEQUENCE: 3
tttcatgttt atcctccc                                          18

<210> SEQ ID NO 4
<211> LENGTH: 29
<212> TYPE: DNA
<213> ORGANISM: Artificial Sequence
<220> FEATURE:
<223> OTHER INFORMATION: Synthetic construct

<400> SEQUENCE: 4
tttcatgttt atcctcccta aacatgaaa                              29

<210> SEQ ID NO 5
<211> LENGTH: 45
<212> TYPE: DNA
<213> ORGANISM: Artificial Sequence
<220> FEATURE:
```

<223> OTHER INFORMATION: Synthetic construct

<400> SEQUENCE: 5
attttgggag gataaacatg aaaacaataa tcttagctag ccgta         45

<210> SEQ ID NO 6
<211> LENGTH: 45
<212> TYPE: DNA
<213> ORGANISM: Artificial Sequence
<220> FEATURE:
<223> OTHER INFORMATION: Synthetic construct

<400> SEQUENCE: 6
attttgggag cataaacatg aaaacaataa tcttagctag ccgta         45

<210> SEQ ID NO 7
<211> LENGTH: 103
<212> TYPE: DNA
<213> ORGANISM: Artificial Sequence
<220> FEATURE:
<223> OTHER INFORMATION: Synthetic construct

<400> SEQUENCE: 7
gacgucaaca caucagauuu ccugguguaa cgaauuuuuu aagugcuucu ugcuuaagca         60
aguuucaucc cgacccccuc agggucggga uuuuuuucaa ttg         103

<210> SEQ ID NO 8
<211> LENGTH: 209
<212> TYPE: DNA
<213> ORGANISM: Artificial Sequence
<220> FEATURE:
<223> OTHER INFORMATION: Synthetic construct

<400> SEQUENCE: 8
gacgtcaaca catcagattt cctggtgtaa cgaatttttt aagtgcttct tgcttaagca         60
agtttcatcc cgaccccctc agggtcggga ttttttcaa ttgctgcagt tgtgtagtct        120
aaaggaccac attgcttaaa aaattcacga agaagaacga attcgttcaa agtagggctg        180
ggggagtccc agccctaaaa aaacttaac         209

<210> SEQ ID NO 9
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(30)
<223> OTHER INFORMATION: n can be any nucleotide

<400> SEQUENCE: 9
caacnnnnnn nnnnnnnnnn nnnnnnnnnn aacg         34

<210> SEQ ID NO 10
<211> LENGTH: 41
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(33)
<223> OTHER INFORMATION: n can be any nucleotide

<400> SEQUENCE: 10
aattcgttnn nnnnnnnnnn nnnnnnnnnn nnngttgacg t                41

<210> SEQ ID NO 11
<211> LENGTH: 49
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(35)
<223> OTHER INFORMATION: n can be any nucleotide

<400> SEQUENCE: 11 aatttttttan nnnnnnnnnn nnnnnnnnnn nnnnntcatc ccgacccccc         49

<210> SEQ ID NO 12
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(43)
<223> OTHER INFORMATION: n can be any nucleotide

<400> SEQUENCE: 12 tgaggggggtc gggatgannn nnnnnnnnnn nnnnnnnnnn nnntaaaa           48

<210> SEQ ID NO 13
<211> LENGTH: 113
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(35)
<223> OTHER INFORMATION: n can be any nucleotide
<220> FEATURE:
<221> NAME/KEY: misc_feature
<222> LOCATION: (49)..(74)
<223> OTHER INFORMATION: n can be any nucleotide

<400> SEQUENCE: 13
gacgtcaacn nnnnnnnnnn nnnnnnnnnn nnnnnaacga auuuuuuann nnnnnnnnnn    60
nnnnnnnnnn nnnnucaucc cgacccccuc agggucggga uuuuuuucaa ttg           113

<210> SEQ ID NO 14
<211> LENGTH: 110
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11)..(35)
<223> OTHER INFORMATION: n can be any nucleotide

<400> SEQUENCE: 14
gacgtcaaca nnnnnnnnnn nnnnnnnnnn nnnnnaacga attttttaag tgcttcttgc    60
ttaagcaagt ttcatcccga cccccctcagg gtcgggattt ttttcaattg               110

<210> SEQ ID NO 15
<211> LENGTH: 106
<212> TYPE: DNA

```
<213> ORGANISM: Artificial Sequence
<220> FEATURE:
<223> OTHER INFORMATION: Synthetic construct
<220> FEATURE:
<221> NAME/KEY: misc_feature
<222> LOCATION: (42)..(67)
<223> OTHER INFORMATION: n can be any nucleotide

<400> SEQUENCE: 15
gacgtcaaca catcagattt cctggtgtaa cgaatttttt annnnnnnnn nnnnnnnnnn      60
nnnnnnntca tcccgacccc ctcagggtcg ggattttttt caattg                   106

<210> SEQ ID NO 16
<211> LENGTH: 33
<212> TYPE: RNA
<213> ORGANISM: Artificial Sequence
<220> FEATURE:
<223> OTHER INFORMATION: Synthetic construct

<400> SEQUENCE: 16
auuucauguu uauucgcucc cuaaacauga aau                                  33

<210> SEQ ID NO 17
<211> LENGTH: 45
<212> TYPE: RNA
<213> ORGANISM: Artificial Sequence
<220> FEATURE:
<223> OTHER INFORMATION: Synthetic construct

<400> SEQUENCE: 17
uuuacauuuu gggcaggcau aauaacgaug aaaacaauaa ucuua                     45

<210> SEQ ID NO 18
<211> LENGTH: 31
<212> TYPE: RNA
<213> ORGANISM: Artificial Sequence
<220> FEATURE:
<223> OTHER INFORMATION: Synthetic construct

<400> SEQUENCE: 18
auuucauguu uauccucccu aaacaugaaa u                                    31

<210> SEQ ID NO 19
<211> LENGTH: 234
<212> TYPE: RNA
<213> ORGANISM: Artificial Sequence
<220> FEATURE:
<223> OTHER INFORMATION: Synthetic construct

<400> SEQUENCE: 19
gggaggauaa acaugaaagg gagcauaaac augaaaggca ggauaaacau gaaagggagc     60
aaaaacauga aaggcaggaa aaacaugaaa ggcagcauaa acaugaaagg cagcaaaaac   120
augaagggga ggaaaaacau gaagggagg auuaacauga aagggaggau aaagaugaaa   180
gggaggauua agaugaaagg gaggauaaac augacaggga ggauaaagau gaca          234

<210> SEQ ID NO 20
<211> LENGTH: 32
<212> TYPE: RNA
<213> ORGANISM: Artificial Sequence
<220> FEATURE:
<223> OTHER INFORMATION: Synthetic construct

<400> SEQUENCE: 20
uauuucaugu uuauccuccc uaaacaugaa au                                   32
```

<210> SEQ ID NO 21
<211> LENGTH: 20
<212> TYPE: RNA
<213> ORGANISM: Artificial Sequence
<220> FEATURE:
<223> OTHER INFORMATION: Synthetic construct

<400> SEQUENCE: 21
auuucauguu uauccuccu                                          20

<210> SEQ ID NO 22
<211> LENGTH: 45
<212> TYPE: RNA
<213> ORGANISM: Artificial Sequence
<220> FEATURE:
<223> OTHER INFORMATION: Synthetic construct

<400> SEQUENCE: 22
uuuacauuuu gggcaggcau aauaacgaug aaaacaauaa ucuua             45

<210> SEQ ID NO 23
<211> LENGTH: 31
<212> TYPE: RNA
<213> ORGANISM: Artificial Sequence
<220> FEATURE:
<223> OTHER INFORMATION: Synthetic construct

<400> SEQUENCE: 23
auuucauguu uauccuccu aaacaugaaa u                             31

<210> SEQ ID NO 24
<211> LENGTH: 45
<212> TYPE: RNA
<213> ORGANISM: Artificial Sequence
<220> FEATURE:
<223> OTHER INFORMATION: Synthetic construct

<400> SEQUENCE: 24
uuuacauuuu gggcaggcau aauaacgaug aaaacaauaa ucuua             45

<210> SEQ ID NO 25
<211> LENGTH: 46
<212> TYPE: RNA
<213> ORGANISM: Artificial Sequence
<220> FEATURE:
<223> OTHER INFORMATION: Synthetic construct

<400> SEQUENCE: 25
uaugaacacu uucauguuua uccucccuaa acaugaaagu guucac            46

<210> SEQ ID NO 26
<211> LENGTH: 44
<212> TYPE: RNA
<213> ORGANISM: Artificial Sequence
<220> FEATURE:
<223> OTHER INFORMATION: Synthetic construct

<400> SEQUENCE: 26
uagaacacuu ucauguuuau ccucccuaaa caugaaagug uucc              44

<210> SEQ ID NO 27
<211> LENGTH: 42
<212> TYPE: RNA
<213> ORGANISM: Artificial Sequence
<220> FEATURE:

<223> OTHER INFORMATION: Synthetic construct

<400> SEQUENCE: 27
uaaacacuuu cauguuuauc cucccuaaac augaaagugu uc                42

<210> SEQ ID NO 28
<211> LENGTH: 40
<212> TYPE: RNA
<213> ORGANISM: Artificial Sequence
<220> FEATURE:
<223> OTHER INFORMATION: Synthetic construct

<400> SEQUENCE: 28
uaacacuuuc auguuuaucc ucccuaaaca ugaaagnguc                  40

<210> SEQ ID NO 29
<211> LENGTH: 38
<212> TYPE: RNA
<213> ORGANISM: Artificial Sequence
<220> FEATURE:
<223> OTHER INFORMATION: Synthetic construct

<400> SEQUENCE: 29
uacacuuuca uguuuauccu cccuaaacau gaaagugc                    38

<210> SEQ ID NO 30
<211> LENGTH: 36
<212> TYPE: RNA
<213> ORGANISM: Artificial Sequence
<220> FEATURE:
<223> OTHER INFORMATION: Synthetic construct

<400> SEQUENCE: 30
uaacuuucau guuuauccuc ccuaaacaug aaaguc                      36

<210> SEQ ID NO 31
<211> LENGTH: 34
<212> TYPE: RNA
<213> ORGANISM: Artificial Sequence
<220> FEATURE:
<223> OTHER INFORMATION: Synthetic construct

<400> SEQUENCE: 31
uacuuucaug uuuauccucc cuaaacauga aagc                        34

<210> SEQ ID NO 32
<211> LENGTH: 33
<212> TYPE: RNA
<213> ORGANISM: Artificial Sequence
<220> FEATURE:
<223> OTHER INFORMATION: Synthetic construct

<400> SEQUENCE: 32
uauuucaugu uuauccuccc auaaacaugg agu                         33

<210> SEQ ID NO 33
<211> LENGTH: 34
<212> TYPE: RNA
<213> ORGANISM: Artificial Sequence
<220> FEATURE:
<223> OTHER INFORMATION: Synthetic construct

<400> SEQUENCE: 33
uauuucaugu uuauccuccc gaugaauaug gagu                        34

-continued

```
<210> SEQ ID NO 34
<211> LENGTH: 36
<212> TYPE: RNA
<213> ORGANISM: Artificial Sequence
<220> FEATURE:
<223> OTHER INFORMATION: Synthetic construct

<400> SEQUENCE: 34
uauuucaugu uuauccuccc ggaugaauga uggagu                                   36

<210> SEQ ID NO 35
<211> LENGTH: 37
<212> TYPE: RNA
<213> ORGANISM: Artificial Sequence
<220> FEATURE:
<223> OTHER INFORMATION: Synthetic construct

<400> SEQUENCE: 35
uauuucaugu uuauccuccc aggugaaug auggaau                                   37

<210> SEQ ID NO 36
<211> LENGTH: 40
<212> TYPE: RNA
<213> ORGANISM: Artificial Sequence
<220> FEATURE:
<223> OTHER INFORMATION: Synthetic construct

<400> SEQUENCE: 36
uauuucaugu uuauccuccc ugaggauuga augauggaau                               40

<210> SEQ ID NO 37
<211> LENGTH: 18
<212> TYPE: DNA
<213> ORGANISM: Artificial Sequence
<220> FEATURE:
<223> OTHER INFORMATION: Synthetic construct

<400> SEQUENCE: 37
tttcatgttt atcctccc                                                       18

<210> SEQ ID NO 38
<211> LENGTH: 23
<212> TYPE: DNA
<213> ORGANISM: Artificial Sequence
<220> FEATURE:
<223> OTHER INFORMATION: Synthetic construct

<400> SEQUENCE: 38
attgttttca tgtttatcct ccc                                                 23

<210> SEQ ID NO 39
<211> LENGTH: 45
<212> TYPE: DNA
<213> ORGANISM: Artificial Sequence
<220> FEATURE:
<223> OTHER INFORMATION: Synthetic construct

<400> SEQUENCE: 39
attttgggag gataaacatg aaaacaataa tcttagctag ccgta                         45

<210> SEQ ID NO 40
<211> LENGTH: 45
<212> TYPE: DNA
<213> ORGANISM: Artificial Sequence
<220> FEATURE:
<223> OTHER INFORMATION: Synthetic construct
```

<400> SEQUENCE: 40
attttgggag cataaacatg aaaacaataa tcttagctag ccgta     45

<210> SEQ ID NO 41
<211> LENGTH: 39
<212> TYPE: DNA
<213> ORGANISM: Artificial Sequence
<220> FEATURE:
<223> OTHER INFORMATION: Synthetic construct

<400> SEQUENCE: 41
attgttttca tgtttatcct ccctaaacat gaaaacaat     39

<210> SEQ ID NO 42
<211> LENGTH: 45
<212> TYPE: DNA
<213> ORGANISM: Artificial Sequence
<220> FEATURE:
<223> OTHER INFORMATION: Synthetic construct

<400> SEQUENCE: 42
attttgggag gataaacatg aaaacaataa tcttagctag ccgta     45

<210> SEQ ID NO 43
<211> LENGTH: 45
<212> TYPE: DNA
<213> ORGANISM: Artificial Sequence
<220> FEATURE:
<223> OTHER INFORMATION: Synthetic construct

<400> SEQUENCE: 43
attttgggag cataaacatg aaaacaataa tcttagctag ccgta     45

<210> SEQ ID NO 44
<211> LENGTH: 39
<212> TYPE: DNA
<213> ORGANISM: Artificial Sequence
<220> FEATURE:
<223> OTHER INFORMATION: Synthetic construct

<400> SEQUENCE: 44
tacactttca tgtttatcct ccctaaacat gaaagtgta     39

<210> SEQ ID NO 45
<211> LENGTH: 39
<212> TYPE: DNA
<213> ORGANISM: Artificial Sequence
<220> FEATURE:
<223> OTHER INFORMATION: Synthetic construct

<400> SEQUENCE: 45
tacattttca tgtttatcct ccctaaacat gaaaatgta     39

<210> SEQ ID NO 46
<211> LENGTH: 39
<212> TYPE: DNA
<213> ORGANISM: Artificial Sequence
<220> FEATURE:
<223> OTHER INFORMATION: Synthetic construct

<400> SEQUENCE: 46
tacgttttca tgtttatcct ccctaaacat gaaaacgta     39

<210> SEQ ID NO 47
<211> LENGTH: 39

```
<212> TYPE: DNA
<213> ORGANISM: Artificial Sequence
<220> FEATURE:
<223> OTHER INFORMATION: Synthetic construct

<400> SEQUENCE: 47
tatgttttca tgtttatcct ccctaaacat gaaaacata                              39

<210> SEQ ID NO 48
<211> LENGTH: 39
<212> TYPE: DNA
<213> ORGANISM: Artificial Sequence
<220> FEATURE:
<223> OTHER INFORMATION: Synthetic construct

<400> SEQUENCE: 48
tttgttttca tgtttatcct ccctaaacat gaaaacaaa                              39

<210> SEQ ID NO 49
<211> LENGTH: 39
<212> TYPE: DNA
<213> ORGANISM: Artificial Sequence
<220> FEATURE:
<223> OTHER INFORMATION: Synthetic construct

<400> SEQUENCE: 49
attgttttca tgtttatcct ccctaaacat gaaaacaat                              39
```